US011000369B2

(12) United States Patent
Gharib et al.

(10) Patent No.: US 11,000,369 B2
(45) Date of Patent: May 11, 2021

(54) SYSTEMS, DEVICES, AND METHODS RELATING TO THE MANUFACTURE OF INTRAVASCULARLY IMPLANTABLE PROSTHETIC VALVES

(71) Applicants: FOLDAX, INC., Salt Lake City, UT (US); CALIFORNIA INSTITUTE OF TECHNOLOGY, Pasadena, CA (US)

(72) Inventors: Morteza Gharib, Altadena, CA (US); Manuel Bedrossian, Tujunga, CA (US); Stephanie Rider, Los Angeles, CA (US); Jason G. Beith, Santa Ana, CA (US)

(73) Assignees: CALIFORNIA INSTITUTE OF TECHNOLGY, Pasadena, CA (US); FOLDAX, INC., Salt Lake City, UT (US)

(*) Notice: Subject to any disclaimer, the term of this patent is extended or adjusted under 35 U.S.C. 154(b) by 0 days.

(21) Appl. No.: 16/215,376

(22) Filed: Dec. 10, 2018

(65) Prior Publication Data

US 2019/0343625 A1 Nov. 14, 2019

Related U.S. Application Data

(60) Provisional application No. 62/699,467, filed on Jul. 17, 2018, provisional application No. 62/698,749, filed on Jul. 16, 2018, provisional application No. 62/597,099, filed on Dec. 11, 2017.

(51) Int. Cl.
*A61F 2/24* (2006.01)

(52) U.S. Cl.
CPC .......... *A61F 2/2415* (2013.01); *A61F 2/2418* (2013.01); *A61F 2/2463* (2013.01); *A61F 2/243* (2013.01); *A61F 2210/0014* (2013.01); *A61F 2250/006* (2013.01)

(58) Field of Classification Search
CPC ............................ A61F 2/2415; A61F 2/2418
USPC .......................................................... 427/2.24
See application file for complete search history.

(56) References Cited

U.S. PATENT DOCUMENTS

| 3,550,206 A | 12/1970 | Von Der Heide |
| 3,964,433 A | 6/1976 | Swartz |
| 3,983,581 A * | 10/1976 | Angell ................... A61F 2/2409 623/2.15 |

(Continued)

FOREIGN PATENT DOCUMENTS

| EP | 2030750 A1 | 3/2009 |
| RU | 2425657 C2 | 8/2011 |

(Continued)

OTHER PUBLICATIONS

EP, 15789241.5 Supplementary Search Report, dated Oct. 27, 2017.

(Continued)

*Primary Examiner* — Cachet I Proctor
(74) *Attorney, Agent, or Firm* — Kurt T. Mulville; VLP Law Group, LLP

(57) ABSTRACT

Improved prosthetic heart valves, their methods of manufacture, and systems and devices for manufacturing the valves are described. The prosthetic heart valves can be configured for transcatheter implantation. The prosthetic heart valves can have artificial leaflets. The prosthetic heart valves can be manufactured in numerous ways, such as by polymeric dipping processes.

18 Claims, 26 Drawing Sheets

(56) References Cited

U.S. PATENT DOCUMENTS

| | | | |
|---|---|---|---|
| 4,222,126 A | 9/1980 | Boretos et al. | |
| 4,265,694 A | 5/1981 | Boretos et al. | |
| 4,291,420 A | 9/1981 | Reul | |
| 4,364,127 A | 12/1982 | Pierce et al. | |
| 4,473,423 A | 9/1984 | Kolff | |
| 4,490,859 A | 1/1985 | Black et al. | |
| 4,506,394 A | 3/1985 | Bédard | |
| 4,556,996 A | 12/1985 | Wallace | |
| 4,626,255 A | 12/1986 | Reichart et al. | |
| 4,759,759 A * | 7/1988 | Walker | A61F 2/2412 |
| | | | 623/2.16 |
| 4,778,461 A | 10/1988 | Pietsch et al. | |
| 4,888,009 A | 12/1989 | Lederman et al. | |
| 5,037,434 A | 8/1991 | Lane | |
| 5,147,391 A | 9/1992 | Lane | |
| 5,258,023 A | 11/1993 | Reger | |
| 5,376,113 A | 12/1994 | Jansen et al. | |
| 5,449,385 A | 9/1995 | Religa et al. | |
| 5,469,868 A * | 11/1995 | Reger | A61F 2/2409 |
| | | | 128/898 |
| 5,489,297 A | 2/1996 | Duran | |
| 5,489,298 A | 2/1996 | Love et al. | |
| 5,500,016 A | 3/1996 | Fisher | |
| 5,549,665 A | 8/1996 | Vesely et al. | |
| 5,653,749 A | 8/1997 | Love et al. | |
| 5,713,953 A | 2/1998 | Vallana et al. | |
| 5,861,028 A | 1/1999 | Angell | |
| 5,928,281 A | 7/1999 | Huynh et al. | |
| 6,117,169 A | 9/2000 | Moe | |
| 6,171,335 B1 | 1/2001 | Wheatley et al. | |
| 6,174,331 B1 * | 1/2001 | Moe | A61F 2/2412 |
| | | | 623/2.12 |
| 6,270,527 B1 * | 8/2001 | Campbell | A61F 2/2409 |
| | | | 623/2.18 |
| 6,283,994 B1 | 9/2001 | Moe et al. | |
| 6,283,995 B1 | 9/2001 | Moe et al. | |
| 6,287,334 B1 | 9/2001 | Moll et al. | |
| 6,334,873 B1 | 1/2002 | Lane et al. | |
| 6,454,798 B1 | 9/2002 | Moe | |
| 6,461,382 B1 | 10/2002 | Cao | |
| 6,475,239 B1 | 11/2002 | Campbell et al. | |
| 6,478,819 B2 | 11/2002 | Moe | |
| 6,562,069 B2 | 5/2003 | Cai et al. | |
| 6,596,024 B2 * | 7/2003 | Chinn | A61L 27/26 |
| | | | 523/112 |
| 6,613,086 B1 | 9/2003 | Moe et al. | |
| 6,666,885 B2 | 12/2003 | Moe | |
| 6,716,244 B2 | 4/2004 | Klaco | |
| 6,755,857 B2 | 6/2004 | Peterson et al. | |
| 6,780,200 B2 | 8/2004 | Jansen | |
| 6,953,332 B1 * | 10/2005 | Kurk | A61F 2/2415 |
| | | | 249/52 |
| 6,984,700 B2 | 1/2006 | Benz et al. | |
| 7,247,167 B2 | 7/2007 | Gabbay | |
| 7,262,260 B2 | 8/2007 | Yilgor et al. | |
| 7,365,134 B2 | 4/2008 | Benz et al. | |
| 7,473,275 B2 | 1/2009 | Marquez | |
| 7,563,280 B2 | 7/2009 | Anderson et al. | |
| 7,641,687 B2 | 1/2010 | Chinn et al. | |
| 7,682,389 B2 | 3/2010 | Beith | |
| 7,776,084 B2 | 8/2010 | Johnson | |
| 7,803,186 B1 | 9/2010 | Li et al. | |
| 7,833,565 B2 | 11/2010 | O'Connor et al. | |
| 7,871,435 B2 | 1/2011 | Carpentier et al. | |
| 7,959,674 B2 | 6/2011 | Shu et al. | |
| 7,988,900 B2 | 8/2011 | Beith | |
| 8,216,631 B2 | 7/2012 | O'Connor et al. | |
| 8,845,720 B2 | 9/2014 | Conklin | |
| 9,301,837 B2 | 4/2016 | Beith | |
| 9,603,707 B2 * | 3/2017 | Li | B29C 41/38 |
| 10,463,478 B2 * | 11/2019 | Bruchman | A61F 2/2409 |
| 10,639,144 B2 * | 5/2020 | Bruchman | A61F 2/2415 |
| 2001/0021872 A1 | 9/2001 | Bailey et al. | |
| 2001/0025196 A1 * | 9/2001 | Chinn | A61L 27/34 |
| | | | 623/2.17 |
| 2002/0062150 A1 | 5/2002 | Campbell et al. | |
| 2002/0082689 A1 * | 6/2002 | Chinn | A61L 27/26 |
| | | | 623/2.17 |
| 2002/0198594 A1 | 12/2002 | Schreck | |
| 2003/0023302 A1 | 1/2003 | Moe et al. | |
| 2003/0055496 A1 | 3/2003 | Cai et al. | |
| 2003/0097175 A1 * | 5/2003 | O'Connor | A61F 2/2412 |
| | | | 623/2.17 |
| 2003/0114913 A1 * | 6/2003 | Spenser | A61F 2/2433 |
| | | | 623/1.11 |
| 2005/0096736 A1 | 5/2005 | Osse et al. | |
| 2005/0113910 A1 | 5/2005 | Paniagua et al. | |
| 2005/0149181 A1 | 7/2005 | Eberhardt | |
| 2006/0047338 A1 | 3/2006 | Jenson et al. | |
| 2006/0122693 A1 * | 6/2006 | Biadillah | A61F 2/2418 |
| | | | 623/1.24 |
| 2006/0167540 A1 * | 7/2006 | Masters | A61L 31/10 |
| | | | 623/1.44 |
| 2006/0184239 A1 | 8/2006 | Andrieu et al. | |
| 2007/0027535 A1 * | 2/2007 | Purdy, Jr. | A61L 27/18 |
| | | | 623/2.18 |
| 2007/0255400 A1 * | 11/2007 | Parravicini | A61F 2/2412 |
| | | | 623/2.41 |
| 2008/0154358 A1 | 6/2008 | Tansley et al. | |
| 2008/0161909 A1 * | 7/2008 | Kheradvar | A61F 2/2436 |
| | | | 623/2.11 |
| 2009/0132035 A1 | 5/2009 | Roth et al. | |
| 2009/0222085 A1 * | 9/2009 | Kumar | A61L 27/507 |
| | | | 623/2.42 |
| 2010/0161045 A1 | 6/2010 | Righini | |
| 2011/0224780 A1 | 9/2011 | Tabor et al. | |
| 2011/0282440 A1 | 11/2011 | Cao et al. | |
| 2012/0035719 A1 * | 2/2012 | Forster | A61F 2/2418 |
| | | | 623/2.14 |
| 2012/0053676 A1 * | 3/2012 | Ku | A61F 2/2412 |
| | | | 623/1.26 |
| 2012/0078347 A1 | 3/2012 | Braido et al. | |
| 2012/0232646 A1 | 9/2012 | Agathos | |
| 2012/0271398 A1 * | 10/2012 | Essinger | A61F 2/2436 |
| | | | 623/1.11 |
| 2013/0096674 A1 | 4/2013 | Iobbi | |
| 2013/0184813 A1 | 7/2013 | Quadri et al. | |
| 2013/0268066 A1 | 10/2013 | Rowe | |
| 2013/0310928 A1 | 11/2013 | Morriss et al. | |
| 2013/0325116 A1 | 12/2013 | Sundler et al. | |
| 2014/0005772 A1 * | 1/2014 | Edelman | A61L 27/18 |
| | | | 623/2.17 |
| 2014/0005773 A1 | 1/2014 | Wheatley | |
| 2014/0012371 A1 | 1/2014 | Li | |
| 2014/0031927 A1 * | 1/2014 | Bruchman | A61F 2/2415 |
| | | | 623/2.18 |
| 2014/0114407 A1 | 4/2014 | Rajamannan | |
| 2014/0167308 A1 | 6/2014 | Li | |
| 2014/0180402 A1 | 6/2014 | Bruchman et al. | |
| 2014/0214158 A1 | 7/2014 | Board et al. | |
| 2015/0119974 A1 * | 4/2015 | Rothstein | A61F 2/2418 |
| | | | 623/1.26 |
| 2015/0119980 A1 | 4/2015 | Beith et al. | |
| 2015/0320554 A1 * | 11/2015 | Beith | A61F 2/2412 |
| | | | 623/2.19 |
| 2016/0214303 A1 | 7/2016 | Gerstenhaber et al. | |
| 2016/0296324 A1 | 10/2016 | Bapat et al. | |
| 2017/0000610 A1 * | 1/2017 | Eppihimer | A61F 2/2412 |
| 2017/0065411 A1 * | 3/2017 | Grundeman | A61F 2/2418 |
| 2017/0071730 A1 * | 3/2017 | Grundeman | A61F 2/2412 |
| 2017/0071735 A1 | 3/2017 | Guttenberg et al. | |
| 2017/0119923 A1 | 5/2017 | Gunatillake et al. | |
| 2017/0189175 A1 * | 7/2017 | Justino | A61F 2/2418 |
| 2018/0116794 A1 | 5/2018 | Beith | |
| 2019/0060061 A1 | 2/2019 | Beith et al. | |
| 2019/0343625 A1 * | 11/2019 | Gharib | A61F 2/2412 |

(56) References Cited

U.S. PATENT DOCUMENTS

FOREIGN PATENT DOCUMENTS

| | | |
|---|---|---|
| WO | WO 2004/019825 A1 | 3/2004 |
| WO | WO 2013/160651 A1 | 10/2013 |
| WO | WO 2014/170870 A2 | 10/2014 |
| WO | WO 2016/098073 A1 | 6/2016 |
| WO | WO 2019/028374 A1 | 2/2019 |

OTHER PUBLICATIONS

WO, PCT/US2015/013980 ISR and Written Opinion, dated May 28, 2015.
WO, PCT/US2017/058588 ISR and Written Opinion, dated Feb. 21, 2018.
WO, PCT/US2018/045202 ISR and Written Opinion, dated Nov. 22, 2018.
WO, PCT/US2018/064792 ISR and Written Opinion, dated Apr. 15, 2019.
Pibarot, P., et al., "Prosthetic Heart Valves: Selection of the Optimal Prosthesis and Long-Term Management", Circulation, 2009, vol. 119, pp. 1034-1048.
Webb, J. G., et al., "Transcatheter Aortic Valve Replacement for Bioprosthetic Aortic Valve Failure: The Valve-in-Valve Procedure", Circulation, 2013, vol. 127, pp. 2542-2550.
Yilgör, E., et al., "Silicone containing copolymers: Synthesis, properties and applications", Progress in Polymer Science, 2014, vol. 39, No. 6, pp. 1165-1195.

* cited by examiner

SYSTEMS, DEVICES, AND METHODS RELATING TO THE MANUFACTURE OF INTRAVASCULARLY IMPLANTABLE PROSTHETIC VALVES

CROSS-REFERENCE TO RELATED APPLICATIONS

This application claims the benefit of and priority to U.S. Provisional Patent Application Ser. No. 62/597,099, filed Dec. 11, 2017, U.S. Provisional Patent Application Ser. No. 62/698,749, filed Jul. 16, 2018, and U.S. Provisional Patent Application Ser. No. 62/699,467, filed Jul. 17, 2018, all of which are incorporated by reference herein in their entireties and for all purposes.

FIELD

The subject matter described herein relates generally to improved replacement valves, and more particularly to improved techniques for the manufacture and manufacturability of prosthetic valves, such as implantable prosthetic heart valves having artificial polymeric leaflets.

BACKGROUND

The human heart has a number of valves for maintaining the flow of blood through the body in the proper direction. The major valves of the heart are the atrioventricular (AV) valves, including the bicuspid (mitral) and the tricuspid valves, and the semilunar valves, including the aortic and the pulmonary valves. When healthy, each of these valves operates in a similar manner. The valve translates between an open state (that permits the flow of blood) and a closed state (that prevents the flow of blood) in response to pressure differentials that arise on opposite sides of the valve.

A patient's health can be placed at serious risk if any of these valves begin to malfunction. Although the malfunction can be due to a variety of reasons, it typically results in either a blood flow restricting stenosis or a regurgitation, where blood is permitted to flow in the wrong direction. If the deficiency is severe, then the heart valve may require replacement.

Substantial effort has been invested in the development of replacement heart valves, most notably replacement aortic and mitral valves. There is currently substantial interest in the transcatheter implantation of prosthetic valves. Transcatheter valve implementations often involve a bioprosthetic valve integrated with an artificial arterial stent. This method offers the advantages of a tissue based valve with the minimally invasive catheter based implantation technique. Examples of such transcatheter implantation techniques include aortic valve replacement techniques, such as transcatheter aortic valve implantation (TAVI) and transcatheter aortic valve replacement (TAVR), and mitral valve replacement techniques such as transcatheter mitral valve implantation (TMVI) and transcatheter mitral valve replacement (TMVR). These techniques involve introducing the valve prosthesis to the patient's body by way of a catheter, and then expanding the prosthesis over the existing damaged heart valve (as opposed to resecting the native valve first). Transcatheter implantations of bioprosthetic valves suffer from the finite life span of the biological tissue used to form the valve leaflets, further exacerbated by the catheter based implantation. In order to fit the valve into a catheter, the valve must be reduced to a smaller cross-sectional size than the size necessary for operation in the aortic or mitral valve position. This size reduction can creases the tissue leaflets, and these creases are susceptible to calcification at a higher rate than uncreased tissue.

For these and other reasons, needs exist for improved implantable valves, and for improved systems, devices, and methods for manufacturing implantable valves.

SUMMARY

Provided herein are a number of example embodiments of prosthetic heart valves configured for implantation through a catheter or other intravascular delivery device. These embodiments generally include a stent or support structure coupled with a valvular body having two or more artificial polymeric leaflets. The prosthetic valves can be contracted to a reduced radial dimension that permits passage through the patient's vasculature or otherwise introduced into the patient's body at a dimension smaller than that required post-implantation. The prosthetic valves can expand, in many embodiments autonomously, to an expanded configuration for operation in regulating the patient's blood flow. The prosthetic valves can be configured as aortic or mitral valve replacements.

Systems, devices, and methods for manufacturing or use in manufacturing a prosthetic heart valve are also provided. Many of these embodiments utilize a dip casting or dipping process that involves immersing some or all of an element of the prosthetic valve (or used in formation of the prosthetic heart valve) into a wet polymer to form a coating of polymer thereon. The polymer can be then be cured to form a coating on a portion of the heart valve or to form a component of the heart valve itself. Numerous variations of method embodiments are disclosed, and these methods themselves can be altered, rearranged, and supplemented with additional steps.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 7-10A are flow diagrams depicting example embodiments of methods of manufacturing valves.

FIGS. 11-13A are flow diagrams depicting example embodiments of methods of manufacturing valves.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The example embodiments described herein relate to improved implantable prosthetic valves, such as prosthetic heart valves having a support structure, stent, or frame coupled with two or more leaflets, and techniques for the manufacture and manufacturability of implantable valves. These embodiments are particularly suited for artificial polymeric leaflets, and the resulting artificial valves offer advantages comparable to current approaches with the added benefit of a longer life span. Valves with polymer-based leaflets are advantageous because polymers can offer the same structural support as biological tissue, while being much thinner and allowing the valve to be more easily contracted for delivery. This in turn results in less stress on the polymer as it is contracted which prevents long-term degradation of the valve leaflets. In addition, the manufacturing methods described herein permit fabrication of a valve without suturing leaflets to a support structure or stent, thus promoting high quality repeatable results.

Example Embodiments of Prosthetic Valves

Figure 1A:
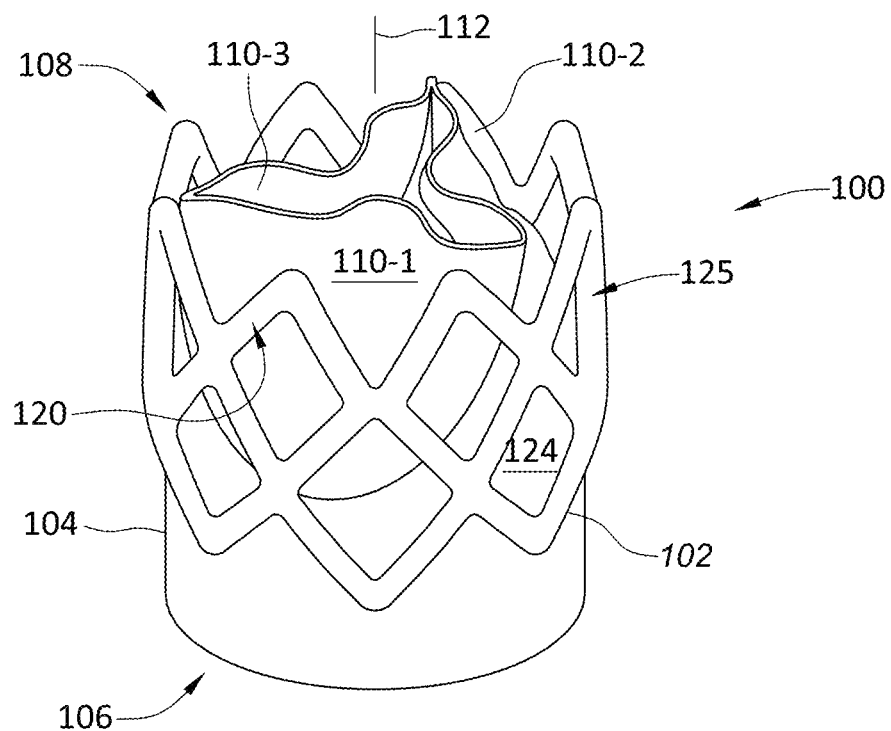
FIG. 1A is a perspective view depicting an example embodiment of a prosthetic valve.

FIG. 1A is a perspective view depicting an example embodiment of an implantable prosthetic valve 100 having a support structure or stent 102 and a valvular body 104. In this embodiment the valvular body is configured as an aortic replacement valve and has three valve leaflets 110-1, 110-2, and 110-3. Valve 100 is configured to allow blood to flow from an upstream end 106 (sometimes referred to as the proximal end) to a downstream end 108 (sometimes referred to as the distal end) and valve 100 has a longitudinal axis 112 extending between upstream end 106 and downstream end 108 parallel to the primary direction of blood flow through the valve.

Figure 1B:
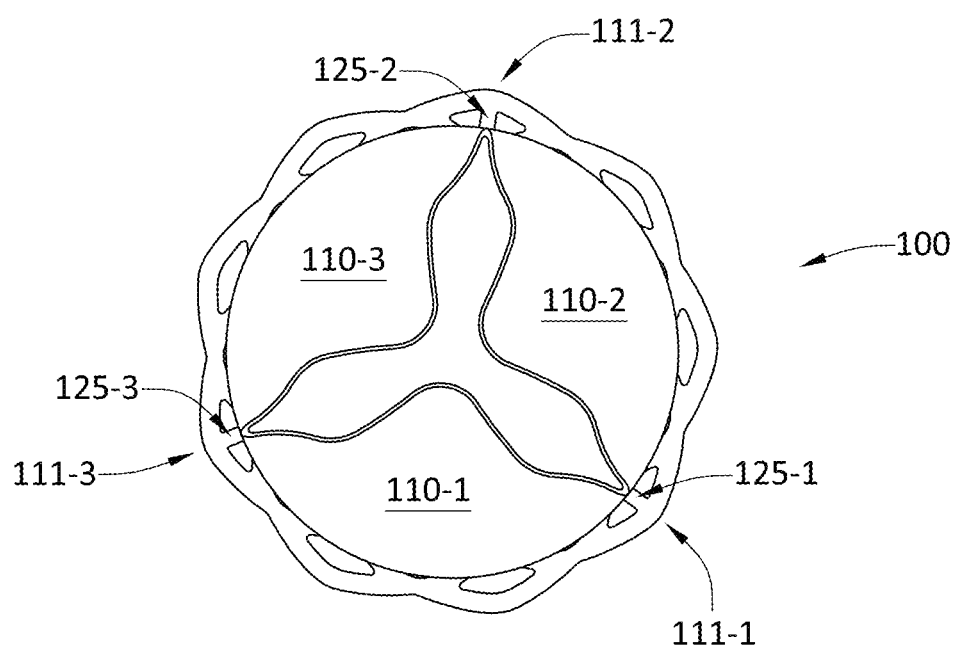
FIG. 1B is a top down view depicting an example embodiment of a prosthetic valve.
Figure 1C:
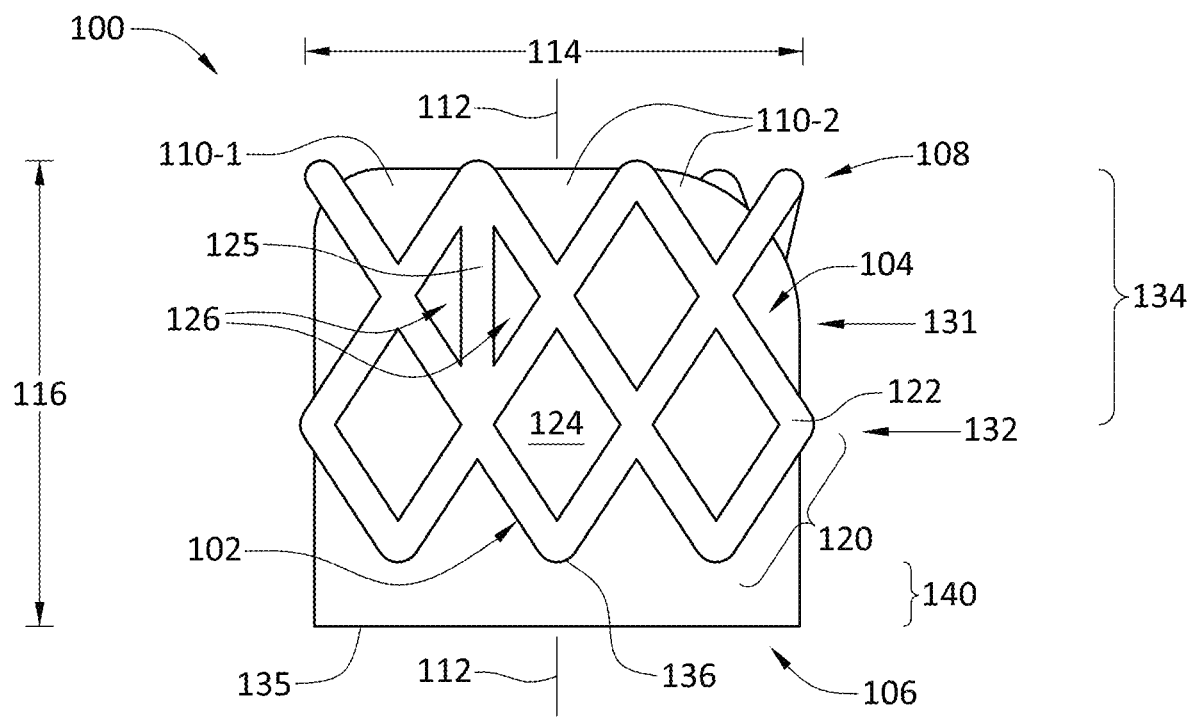
FIGS. 1C-1D are side views depicting an example embodiment of a prosthetic valve in expanded and contracted states, respectively.
Figure 1D:
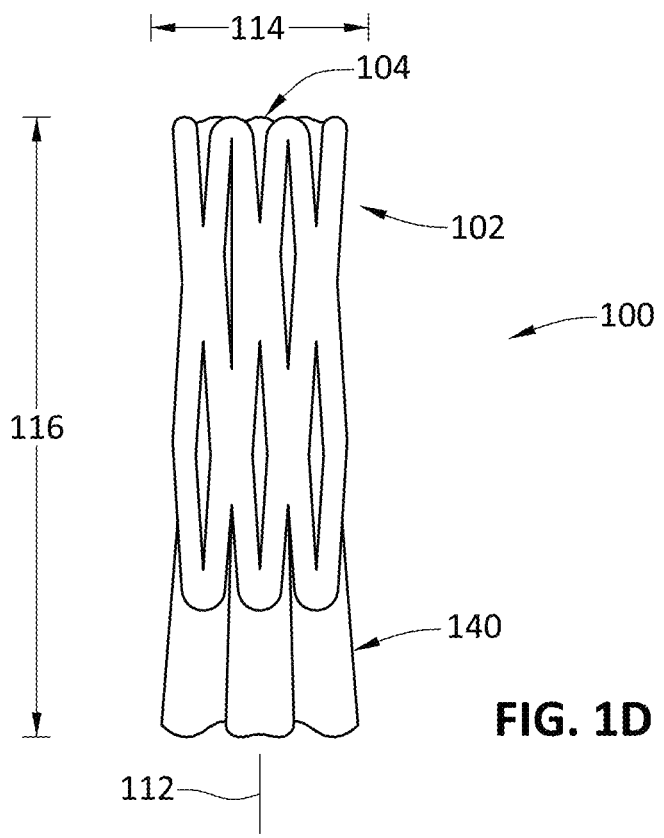
Figure 1E:
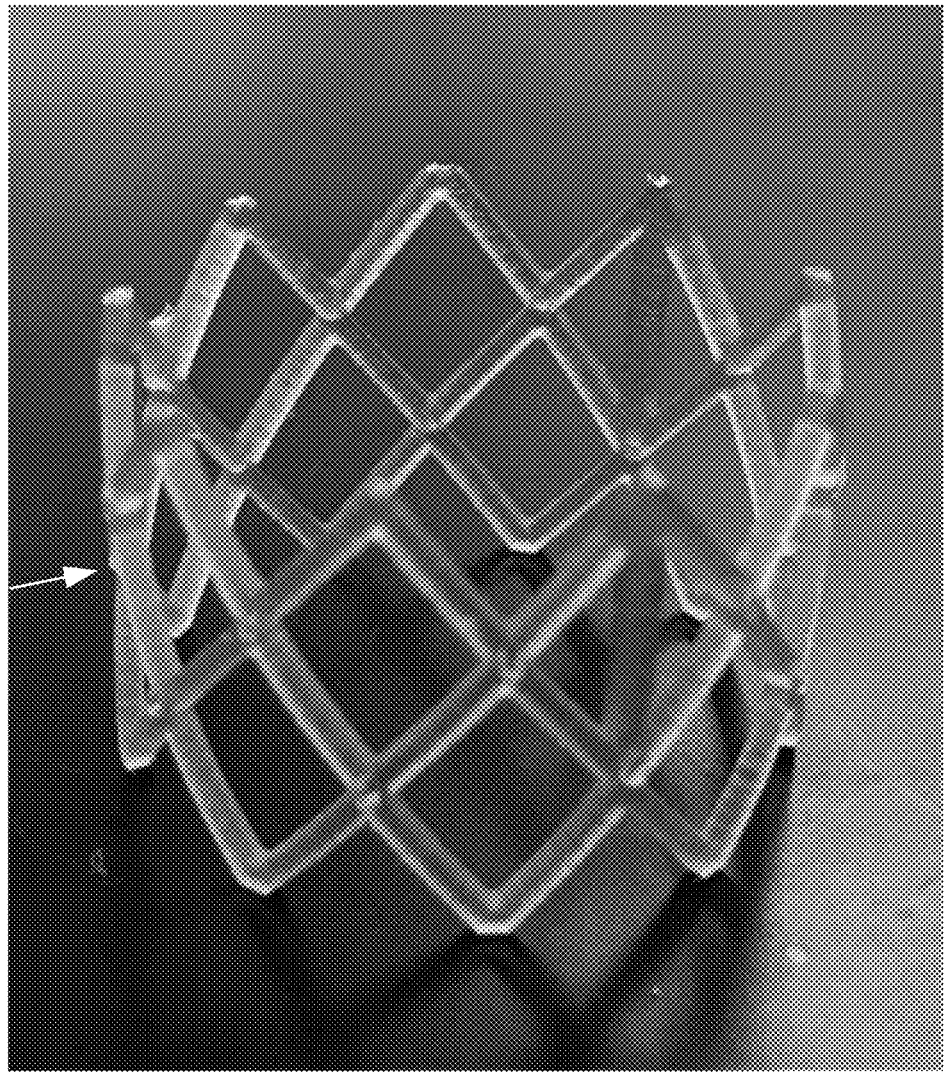
FIG. 1E is a photograph depicting an example embodiment of a stent of a prosthetic valve.

All embodiments of valve 100 described herein can be configured for transcatheter implantation, and thus can transition between, on the one hand, an expanded or operative configuration (having a relatively larger radial dimension) for regulating blood flow and, on the other hand, a contracted or deliverable configuration (having a relatively smaller radial dimension) that permits intravascular delivery. FIG. 1B is an end view depicting downstream end 108 of valve 100 in the expanded configuration (with leaflets 110 in a partially open at-rest state) with the radial dimension or width of valve 100 indicated by reference 114. FIGS. 1C and 1D are side views depicting valve 100 in the expanded and contracted configurations, respectively. The longitudinal dimension or length of valve 100 is indicated by reference 116. Valve 100 has a relatively larger radial dimension 114 and a relatively smaller longitudinal dimension 116 in the expanded configuration of FIG. 1C than in the contracted configuration of FIG. 1D, where valve 100 is longitudinally lengthened and radially shortened. FIG. 1E is a photograph depicting an example embodiment of stent 102 in isolation.

Stent 102 is coupled with valvular body 104 and provides radial and longitudinal support for body 104. In the embodiment of FIGS. 1A-1E, the body of stent 102 includes multiple struts 120 coupled together in a unitary or monolithic body. Each strut 120 is coupled with another strut at a location 122 that is deformable for transition of stent 102 between the expanded and contracted states. In this embodiment, struts 120 are interconnected in a crossing pattern, or lattice, such that multiple open regions 124 are present. These open regions 124 have a four-sided diamond shape in the configuration shown here. In the expanded state shown in FIG. 1C, each strut 120 is oriented at an angle with respect to longitudinal axis 112, with the exception of strut 125, which is an optional strut located parallel with longitudinal axis 112.

Strut 125 provides additional support (e.g., resistance to tensile, compressive, and lateral force) at the position on stent 102 corresponding to the commissure position where leaflets 110-1 and 110-2 meet. These positions on stent 102 are indicated in FIG. 1B by reference numeral 111. Two triangular-shaped open regions 126 are present on each side of strut 125. Each set of struts 120 and 125 forming an individual open region 124 or 126 can be referred to as a cell of stent 102, and the struts 120 and 125 can be part of two or more cells. Struts 125 can provide resistance to deflection of the downstream portion of valve 100 when in the closed state, and can provide increased surface area for bonding or coupling the polymer of valvular body 104 to stent 102.

In this embodiment there are two rows of cells indicated by reference numerals 131 and 132, where each row includes nine cells, although this is only an example and the rows can have other numbers of cells as stated below. Leaflets 110 are located adjacent the downstream row 131 of cells, generally in region 134. The upstream terminus 135 of valvular body 104 can be at various locations with respect to the upstream terminus 136 of stent 102. In this embodiment, the upstream terminus 135 of valvular body 104 is in a position farther upstream (or proximal) to upstream terminus 136 of stent 102 such that a length of valvular body 104 exists upstream to stent 102. This upstream portion of valvular body 104 can be referred to as a skirt 140. Skirt 140 can prevent or resist paravalvular leakage in some embodiments, and can also be placed over stent 102 to cover any sharp or abrasive edges that can otherwise introduce stress concentration to the valve as well as traumatize the surrounding tissue. In addition to the manufacturing techniques described herein (e.g., dipping and injection molding), skirt 140 can be formed by electrospinning the polymer.

In the contracted configuration of FIG. 1D, stent 102 and valvular body 104 are both radially contracted causing open regions 124 and 126 to become at least partially closed, and in most cases substantially closed. In this contracted configuration, each strut 120 moves to an orientation that is closer to parallel to longitudinal axis 112 than in the expanded configuration. Valve 100 can be configured such that the longitudinal axis of each of the plurality of struts 120 are parallel to longitudinal axis 112 of the valve or substantially parallel (e.g., about 5 degrees or less) to longitudinal axis 112 when valve 100 is in the fully contracted configuration. In the contracted configuration valvular body 104 can fold or collapse upon itself radially, and also elastically deform longitudinally to permit longitudinal lengthening of stent 102. Upon expansion, valvular body 104 can elastically return to its original shape.

Figure 2A:
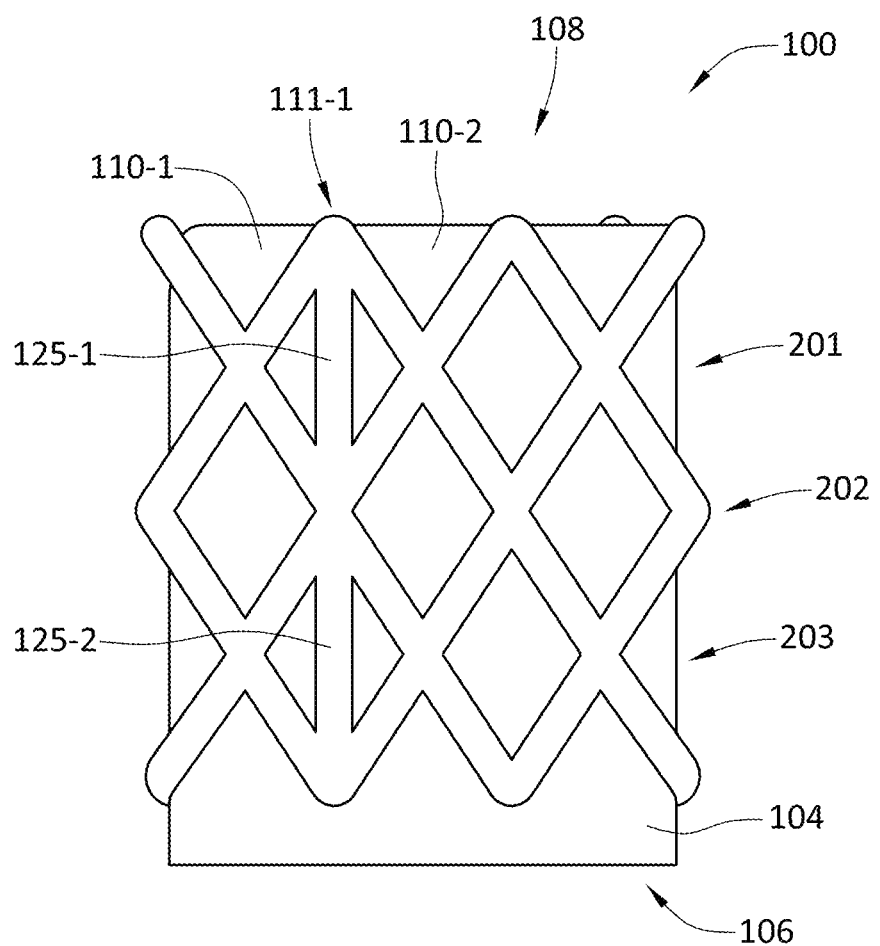
FIGS. 2A-2B are side views depicting an example embodiment of a prosthetic valve in expanded and contracted states, respectively.
Figure 2B:
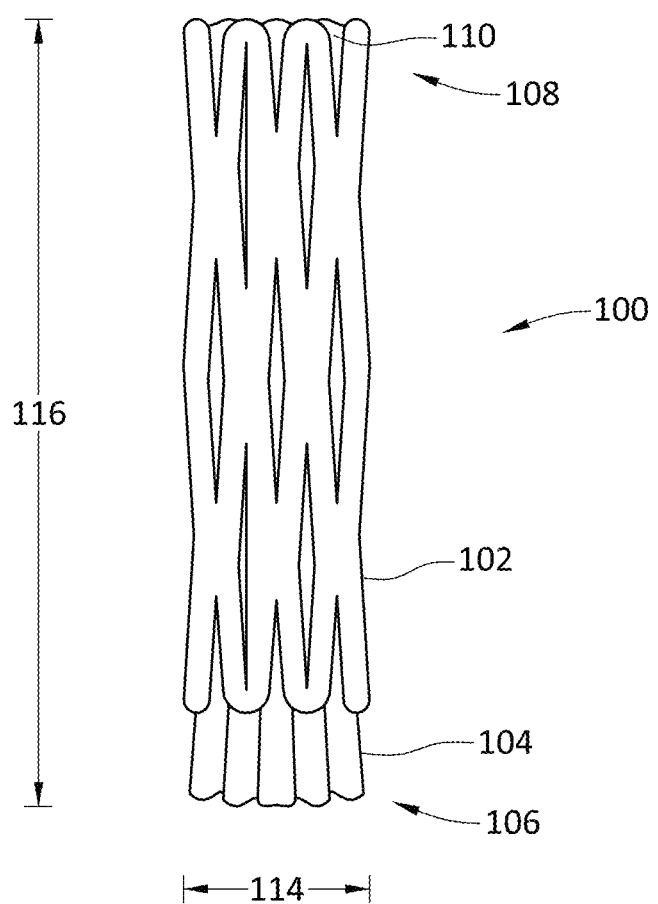

FIGS. 2A and 2B are side views of another example embodiment of valve 100 in the expanded and contracted states, respectively. Here, valve 100 includes three rows of cells 201-203. A first vertical strut 125-1 is present in the first row 201 of cells to provide additional support at commissure position 111-1 where leaflets 110-1 and 110-2 meet. A second strut 125-2 is present in the third row of cells 203, directly upstream to first strut 125-2, to provide additional support at location 111-1. Both first and second struts 125-1 and 125-2 are optional, and each is preferably elastic to permit longitudinal lengthening of stent 102 during contraction. Although not shown, similar struts 125 are also present at positions 111-2 and 111-3. Embodiments of valve 100 can have zero, one, or more struts 125 at each of the locations 111 where leaflets 110 meet. Embodiments of valve 100 can also have only one row of cells, or two or more rows of cells, and each row can include any number of two or more cells. In many embodiments each row includes a number of cells that is an integer multiple of the number of leaflets.

Figure 2C:
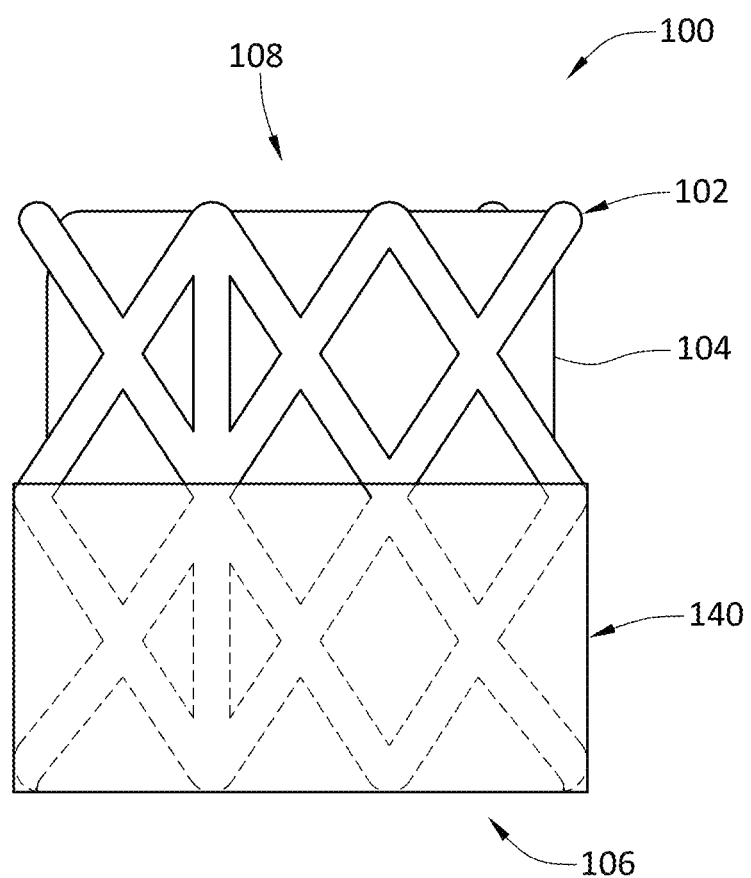
FIG. 2C is a side view depicting an example embodiment of a prosthetic valve.

FIG. 2C depicts a side view of another example embodiment of valve 100 similar to that of FIGS. 2A and 2B, except skirt 140 has been placed (e.g., rolled or inverted) over the upstream side of stent 102. Such a configuration can resist paravalvular leakage between valve 100 and the adjacent tissue, and also protect the tissue against relative sharp or traumatic edges of stent 102. Skirt 140 can be placed over any desired length of stent 102 (e.g., 10%, 25%, 50%, 75%, 100%). If stent 102 is metallic and skirt 140 is placed over the entire length of stent 102, then skirt 140 can also function to electrically insulate stent 102. Skirt 140 can be bonded (e.g., through curing of the polymer or otherwise) to the exterior of the upstream side or portion of stent 102, or can rest on the exterior upstream side without being bonded thereto.

Valve 100 can be carried in the contracted configuration within a lumen of a tubular, elongate delivery device (e.g., a catheter) or restrained in the contracted configuration and carried on the outer diameter of the delivery device, which in turn can be tubular or non-tubular. Valve 100 can be biased to autonomously expand from the contracted configuration to the expanded configuration upon release from the constraint imposed by the delivery device (sometimes referred to as a "self-expanding" valve). Both stent 102 and valvular body 104 can be an elastic material that returns to the expanded configuration after contraction. Alternatively, stent 102 can be elastic and serve as the primary or sole bias to return valve 100 to the expanded configuration. Valve 100 can also be configured to require the application of external force (such as from a balloon or other mechanism) to cause expansion to the expanded configuration.

Figure 3B:
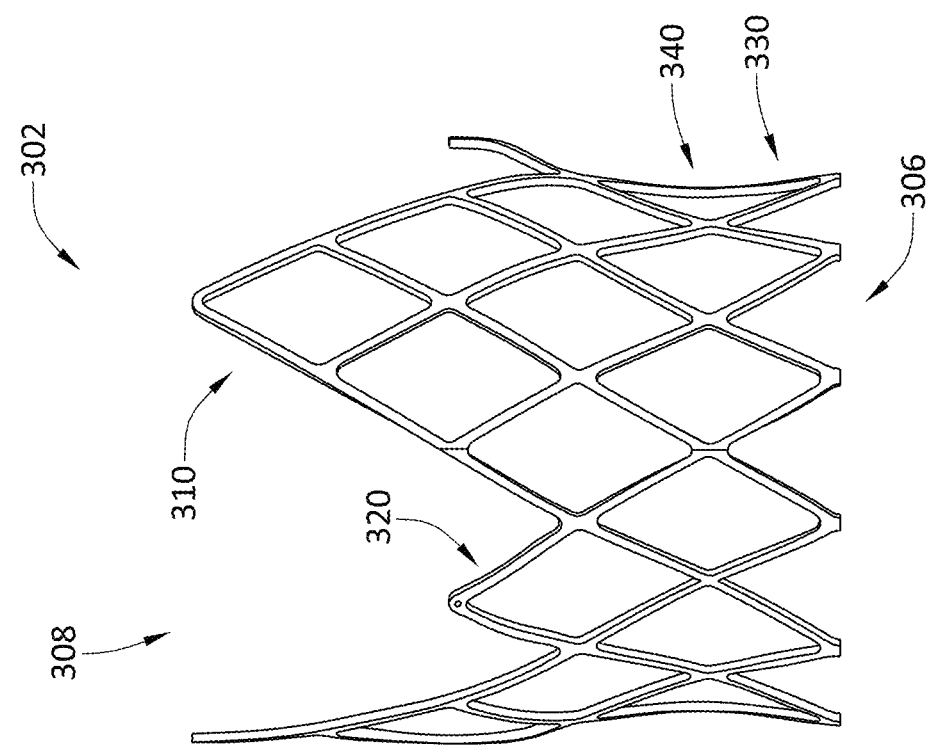
FIG. 3B is a side view of the front half of an example embodiment of a stent of a prosthetic valve in an expanded state.
Figure 3A:
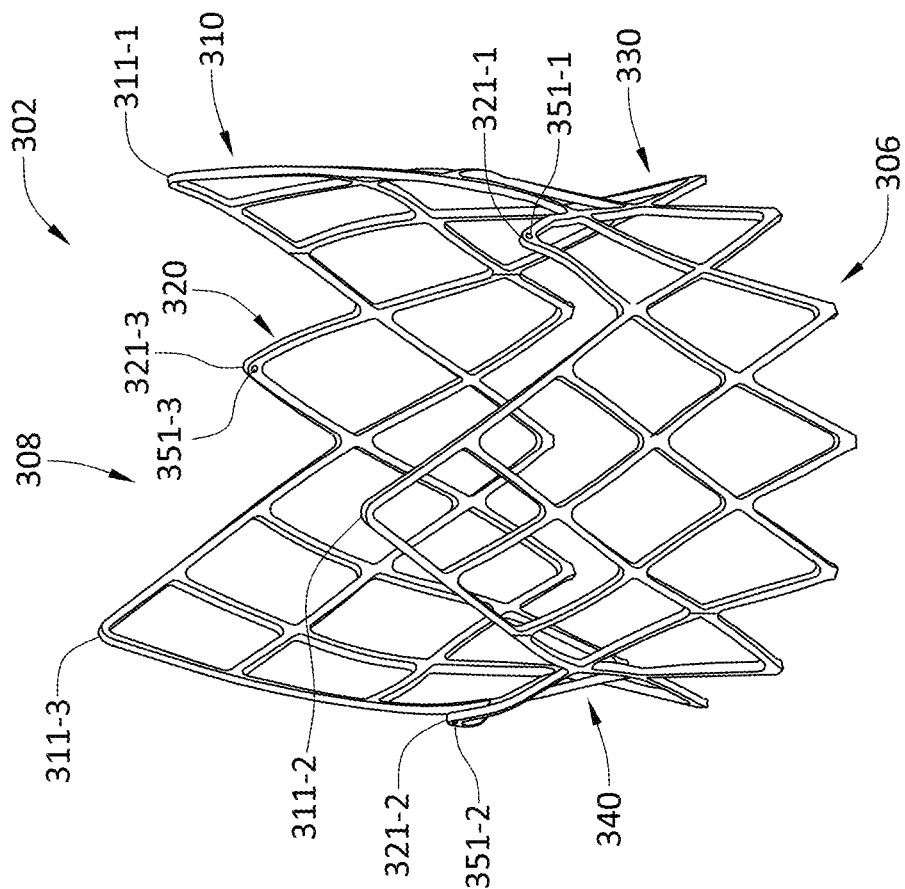
FIG. 3A is a perspective view of an example embodiment of a stent of a prosthetic valve in an expanded state.
Figure 3C:
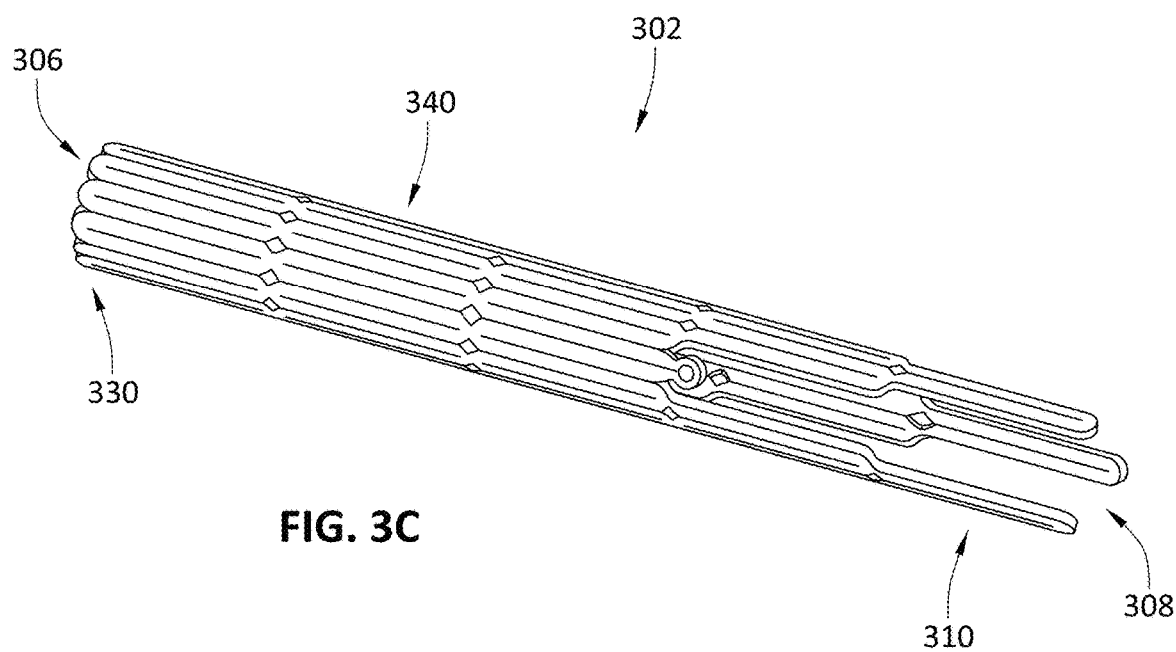
FIGS. 3C-3D are perspective and side views, respectively, of an example embodiment of a stent of a prosthetic valve in a contracted state.
Figure 3D:
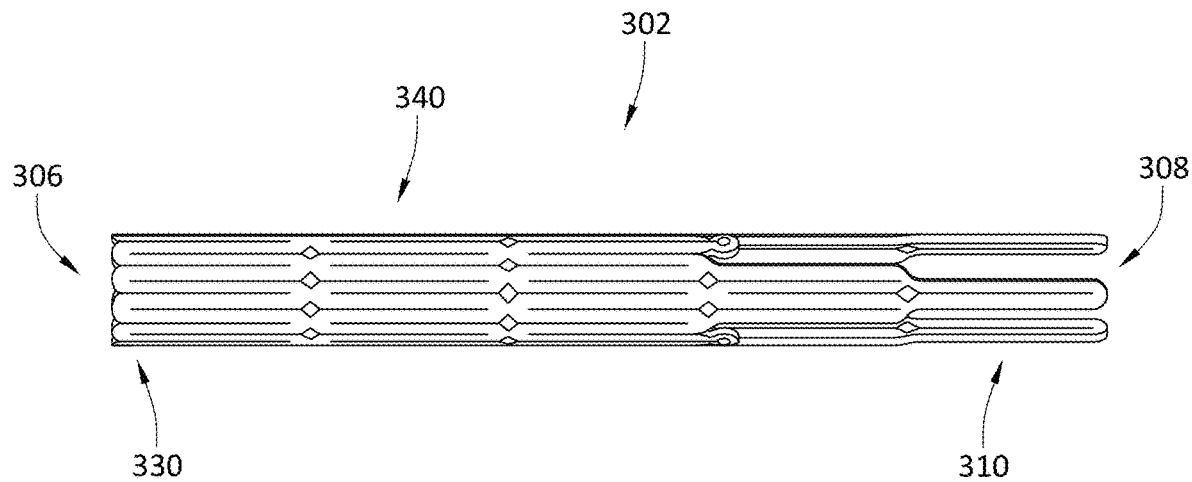
Figure 3F:
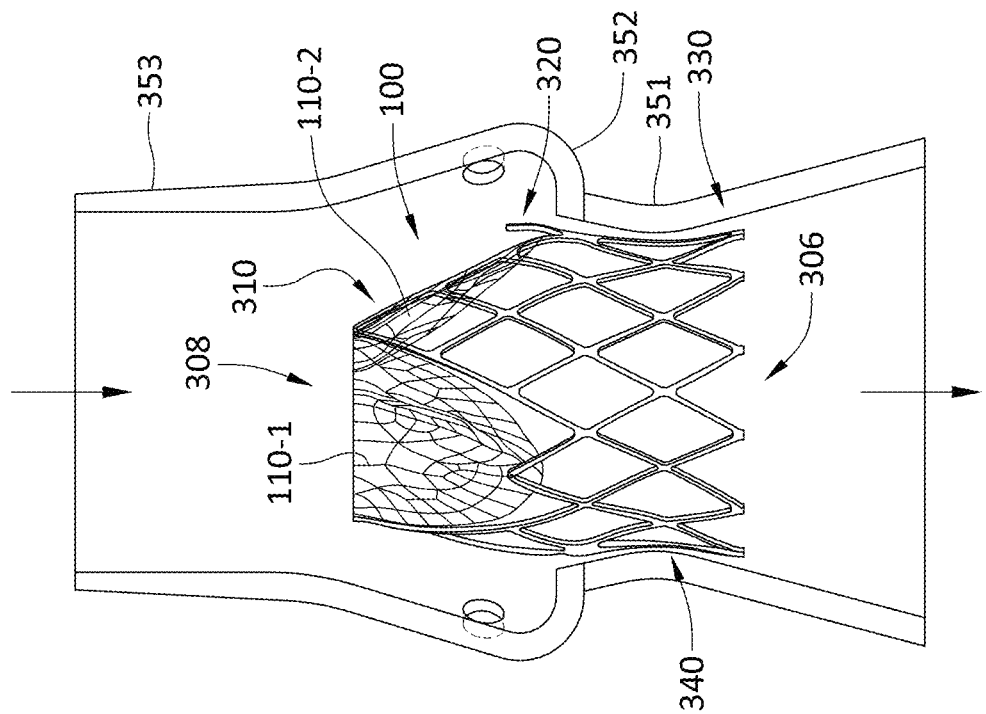
FIGS. 3E-3F are partial cross-sectional views depicting the front half of an example embodiment of a valve within a cross-section of the aortic anatomy when the valve is in the open and closed states, respectively.
Figure 3E:
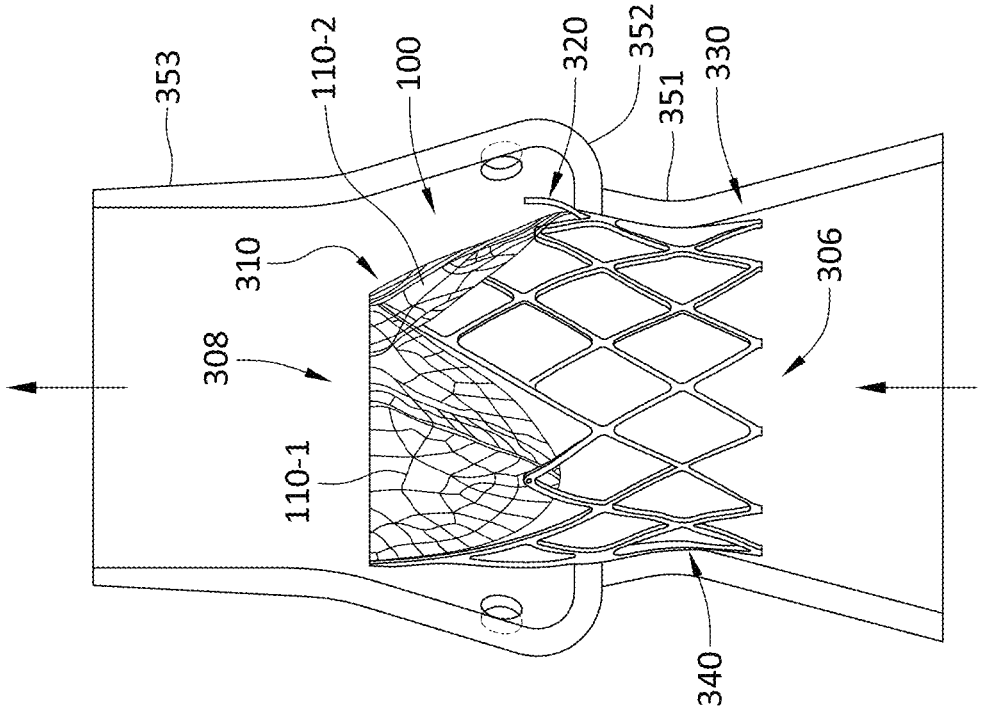

Another example embodiment of valve 100 is described with respect to FIGS. 3A-3F, where valve 100 includes a contoured stent 302 coupled with valvular body 104. FIGS. 3A-3B are perspective and side views, respectively, of stent 302 in the expanded state (without valvular body 104), FIGS. 3C-3D are perspective and side views, respectively, of stent 302 in the contracted state (without valvular body 104), and FIGS. 3E-3F are cross-sections of the aortic anatomy depicting side views of valve 100 within that anatomy while in the open and closed states, respectively.

In this example embodiment, stent 302 is a self-expanding frame of non-uniform radius having an upstream (proximal) end 306 and a downstream (distal) end 308. Downstream end 308 has a first (or primary) crown 310 as well as a second (or secondary) crown 320 that can extend radially outward farther than primary crown 310. Primary crown 310 extends farther distally than secondary crown 320. A third (or tertiary) crown 330 is located at upstream end 306 of stent 302. A necked down region (or waist) 340 is present between crown 330, on the one hand, and crowns 310 and 320, on the other hand. Waist 340 is where stent 302 has the relatively smallest radial width. Each of crowns 310, 320, and 330 extends radially outwards (e.g., flares) from waist 340.

Primary crown 310 is a continuation of the lattice arrangement of stent 302 and includes three crown segments 311-1, 311-2, and 311-3 in locations where adjacent leaflets (not shown) meet. Primary crown 310 mimics the tri-leaflet geometry of a natural heart valve in order to provide optimal attachment of artificial leaflets 110 (FIGS. 3E-3F). Bioprosthetic (natural tissue) leaflets can alternatively be attached (e.g., sutured) onto stent 302. The tri-leaflet geometry ensures a high effective orifice area (EOA). By mimicking the natural shape of a heart valve, the stresses associated with normal operating conditions of the valve material are more evenly spread across stent 302, increasing the overall longevity of the device. Primary crown 310 also mimics the compliance of natural heart valve attachment sites by deflecting, which further distributes stress associated with systolic cycle loading over valve 100. This deflection also allows easier access for blood to flow through the aortic sinuses.

Secondary crown 320 is also a continuation of the regular lattice of stent 302 and includes three crown segments 321-1, 321-2, and 321-3 that flare outwardly to a greater extent that primary crown 310 (see FIG. 3B). Each secondary crown segment 321 assists in fixation of valve 100 within the anatomy. Segments 321 also include alignment holes 351 (e.g., in the distal most strut) that can receive a thread, tether, or other portion of a delivery device and can be used to physically manipulate the position of valve 100 in three-dimensional space, as well as to radially rotate or tilt valve 100 during implantation. Such control assists the medical professional in achieving precise alignment. Alignment holes 351 can also be used for device retrieval if the surgeon should need to re-align the device after deployment.

Tertiary crown 330 located on the proximal end of the frame has a slight outward expansion that assists in fixation. Stent 302 has the ability to self-locate within the anatomy when used as, e.g., an aortic or mitral valve. For example, when configured as an aortic replacement valve, waist 340 is receptive to placement immediately adjacent the aortic annulus.

FIGS. 3E and 3F depict this embodiment of valve 100 configured as an aortic valve and deployed within the aortic anatomy with valve 100 in the open and closed states, respectively. Waist 340 of valve 100 is adjacent annulus 351 (which bulges into the interior of the aorta) with primary crown 310 and secondary crown 320 located downstream of annulus 351 in the ascending aorta 353, and tertiary crown 330 located upstream of annulus 351. Valve 100 is sized such that the radial dimension of the crowns 310, 320, and 330, exceeds the radial dimension of annulus 351 and waist 340 when waist 340 is expanded in the anatomy. Valve 100 may be slightly oversized to ensure adequate fixation, and may not expand to the maximum radial dimension when implanted.

Valve 100 has a compliant nature. During flow conditions (FIG. 3E) leaflets 110 are open and allowing flow, but when valve 100 closes (FIG. 3F) crown segments 311 of primary crown 310 deflect radially inwards allowing blood to flow easily into and though aortic sinuses 352. Crown segments 321 of secondary crown 320 can also deflect inwards to a lesser degree without impacting the fixation of valve 100.

The embodiments of valve 100 described herein are arrived at by accounting for design considerations such as minimization of the overall size of stent 102 and 302, prevention of interference with the electrical conduction pathways of the heart, minimization of the fluidic pressure gradient across valve 100, as well as the prevention of blockage of any of the three aortic sinuses. By way of non-limiting example, in the embodiment of FIGS. 3A-3F, the overall aspect ratio (length and width) can be about 1:1 and the ratio of primary crown height to overall length can be about 1:2. These aspect ratios can be modulated as needed depending on various factors related to the patient as well as whether valve 100 is intended as an aortic or mitral replacement. The acute opening angle of each crown segment of both the secondary and tertiary crowns can be 50° and can vary up to and including 60° to promote the stents ability to be crimped and placed inside a delivery device while at the same time providing enough radial force to sufficiently fix valve 100 in the ventricular outflow tract (VOT). Many embodiments of valve 100 can be contracted such that the circumference is reduced by 84% or more. Additional rows of cells may also be added for additional stability in the VOT as well as to increase the radial force stent 102 or 302 exerts on the surrounding tissue.

The embodiment of valve 100 described with respect to FIGS. 3A-3F differs from the embodiments of FIGS. 1A-2C primarily in the contoured profile and the presence of multiple downstream crowns, but all other features and variations of valve 100 described with respect to FIGS. 1A-2C can likewise be applied to the example embodiment of FIGS. 3A-3F.

While the embodiments of valve 100 have a generally right cylindrical upstream end, these embodiments can alternatively have a curved or scalloped upstream end. Scalloped ends are known to those of skill in the art (see, e.g., U.S. Pat. No. 9,301,837, which is incorporated by reference herein in its entirety and for all purposes.

In all of the embodiments of stent 302, secondary crown 320 and/or tertiary crown 330 can be omitted if desired. Alternatively, either or both of crowns 320 and 330 can be included but can have a constant radius along their length such that the sides of stent 302 where crowns 320 and/or 330 are present are parallel to the longitudinal axis of stent 302.

While not required, stents 102 and 302 are preferably fabricated in stages from one or more materials (e.g., a primary or core structure of one material with a secondary structure or coating of the same or another material). The material for the primary structure is preferably elastic or superelastic. Examples of such materials include titanium alloys (e.g., nitinol), elgiloy, stainless steel, and various polymers. Materials for the secondary coating can include polymeric materials such as polyether ether ketones (PEEK), polyurethanes, a polyetherimides (PEI) such as ULTEM, any of the artificial materials used to form leaflets 110, and others. Leaflets 110 can be fabricated from polymeric materials, including any biostable polyurethanes and polyurethane compositions (e.g., polysiloxane-containing polyurethanes, etc.) known in the art. Examples of polyurethane-containing leaflets are described in U.S. Pat. Nos. 6,984,700, 7,262,260, 7,365,134, U.S. Patent Publ. No. 2017/0119923 ("Polyurethane/urea Compositions"), and Yilgor et al., "Silicone containing copolymers: Synthesis, properties and applications," Prog. Polym. Sci. (2013), all of which are incorporated by reference herein in their entirety for all purposes. Materials that approach ideal isotropic non-creeping characteristics are particularly suitable for use in many embodiments. Leaflets 110 can also be fabricated from biological tissue (e.g., a porcine valve).

Example Embodiments of Prosthetic Valve Manufacturing

Numerous embodiments of systems, devices, and methods of manufacturing valves 100 having artificial polymeric leaflets 110 are described herein. These systems, devices, and methods can be applied to any stent geometry or polymer, extending the valve's possible applications to involve the treatment of multiple conditions simultaneously, such as incorporating drug eluting technologies to reduce inflammation due to the foreign body response of the recipient's immune system. In addition, the manufacturing methods described here can be automated and/or robotized for inexpensive and repeatable manufacturing.

Generally, the manufacturing methods involve the fabrication of stent 102 or 302 and then either coupling leaflets 110 or valvular body 104 thereto, or integrally forming leaflets 110 thereon. For ease of discussion these systems, devices, and methods are described herein with respect to fabrication of a valve 100 having stent 102, however it is stressed that all such systems, devices, and methods can likewise be used to fabricate embodiments of valve 100 having contoured stent 302. The manufacturing embodiments described herein utilize a dip casting or dipping process, however those of ordinary skill in the art will recognize that other comparable formation processes (e.g., molding) can be used instead. Dipping is used because the uniform effect of gravity onto the polymer as it cures ensures that the resulting mold is created at the lowest energy state of the polymer. This eliminates stress concentrations in the macro and micro-structure of the polymer that can result from other common molding techniques such as injection molding, thus greatly extending the valve's lifespan.

The use of these dipping techniques in addition to the use of a contractable stent structure more readily allows valve 100 to be implanted in a non-invasive catheter based procedure because the stent will retain the ability to be contracted or crimped into a smaller diameter than its resting size.

FIGS. 4A-4F are photographs of various stages of valve manufacturing that will be referenced in conjunction with described the present embodiments. FIGS. 4A-4F are examples of manufacturing primarily by hand (manually), but these stages can be automated for use in a higher volume manufacturing line. The manufacturing embodiments described herein can utilize any of the approaches described in Int'l Patent Application PCT/US18/45202 filed Aug. 3, 2018 and titled "Systems, Devices, and Methods Relating to the Manufacture of Prosthetic Valves," which is incorporated by reference herein in its entirety and for all purposes. These approaches include, by way of non-limiting example: the use of a two-stage polymer curing process and/or the use of an environmental humidity chamber (EHC) for curing polymer for the stent and/or valvular body of valve 100; and/or the application of an identifier (e.g., a bar code) for improved traceability and/or automation.

Figure 4B:
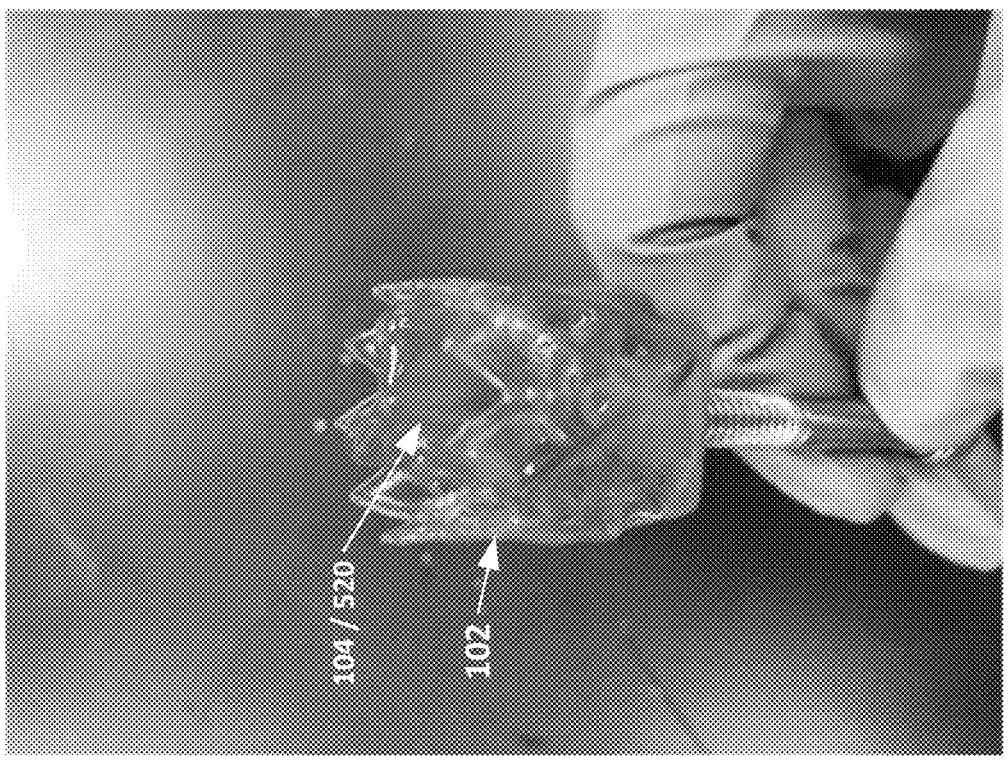
FIGS. 4A-4F are photographs of examples of various stages of valve manufacturing processes.
Figure 4A:
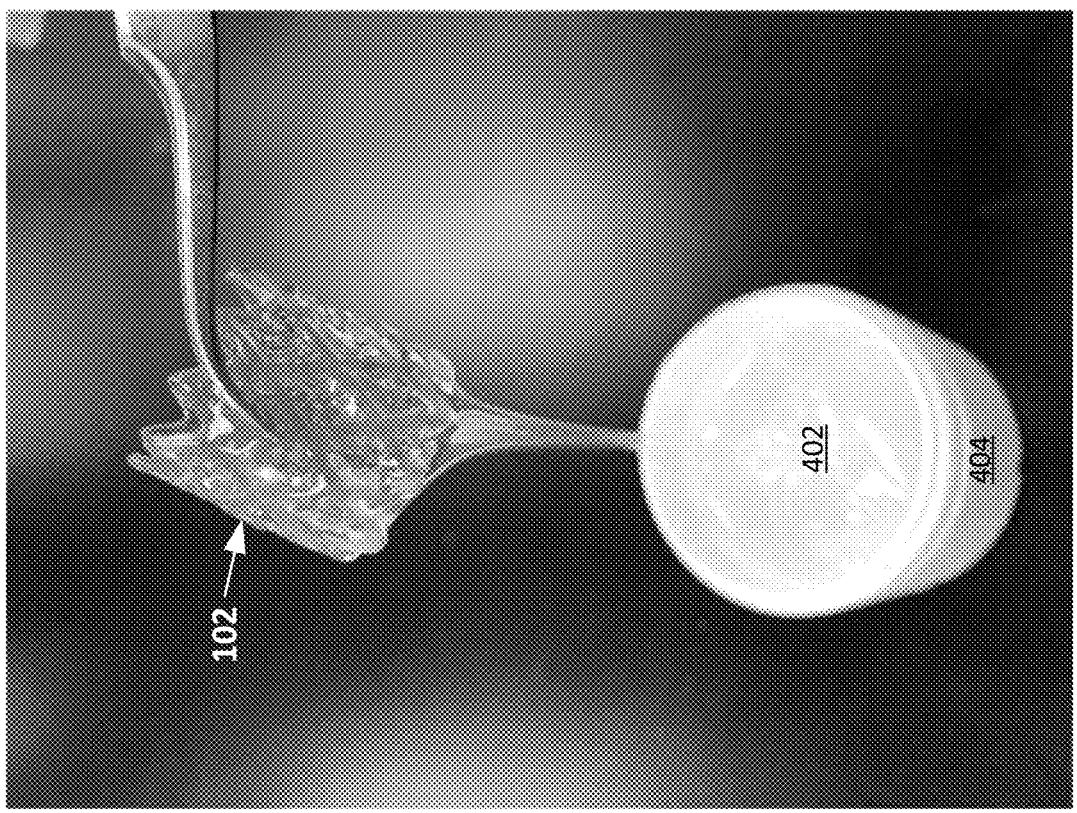
Figure 5A:
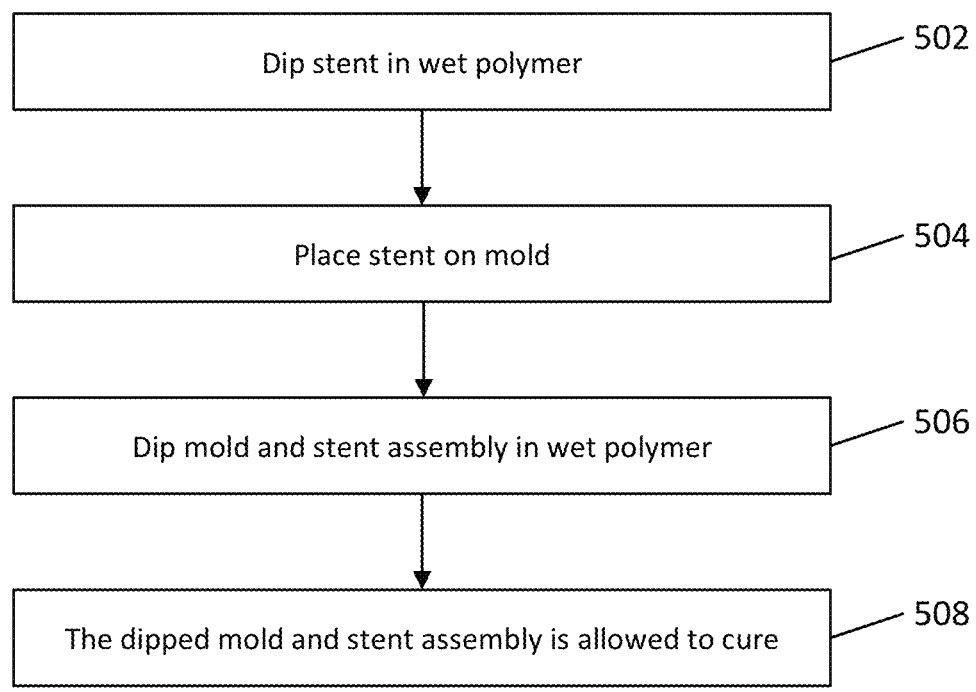
FIG. 5A is a flow diagram depicting an example embodiment of a method of manufacturing a valve.

FIG. 5A is a flow diagram depicting an example embodiment of a method 500 of manufacturing valve 100. At 502, stent 102 is dipped in a wet polymer 402 contained within a vessel 404 (FIG. 4A). In this and all dipping stages described herein, the actual movement of the structure into the wet polymer can be automated with a computer-controlled device. As used herein, "dipping" refers to the acts of placing the element to be dipped (e.g., stent, mold, valve) into the wet polymer and subsequently removing it. The dipping can be performed such that at least one end, but preferably all of stent 102 is coated or encapsulated in the polymer. Stent 102 can be partially cured to allow excess polymer to run off, or stent 102 can proceed directly (without curing) to 504. At 504, preferably while stent 102 is still wet (at least readily deformable and removable upon touching), stent 102 can be placed onto a mold 520 configured to form valvular body 104 and leaflets 110. Mold 520 can also be referred to as a former or mandrel and can be shaped cylindrically or in any other desired fashion to produce the components of valve 100. Mold 520 can have a contoured surface for formation of valve leaflets 110, although such is not required.

Figure 5C:
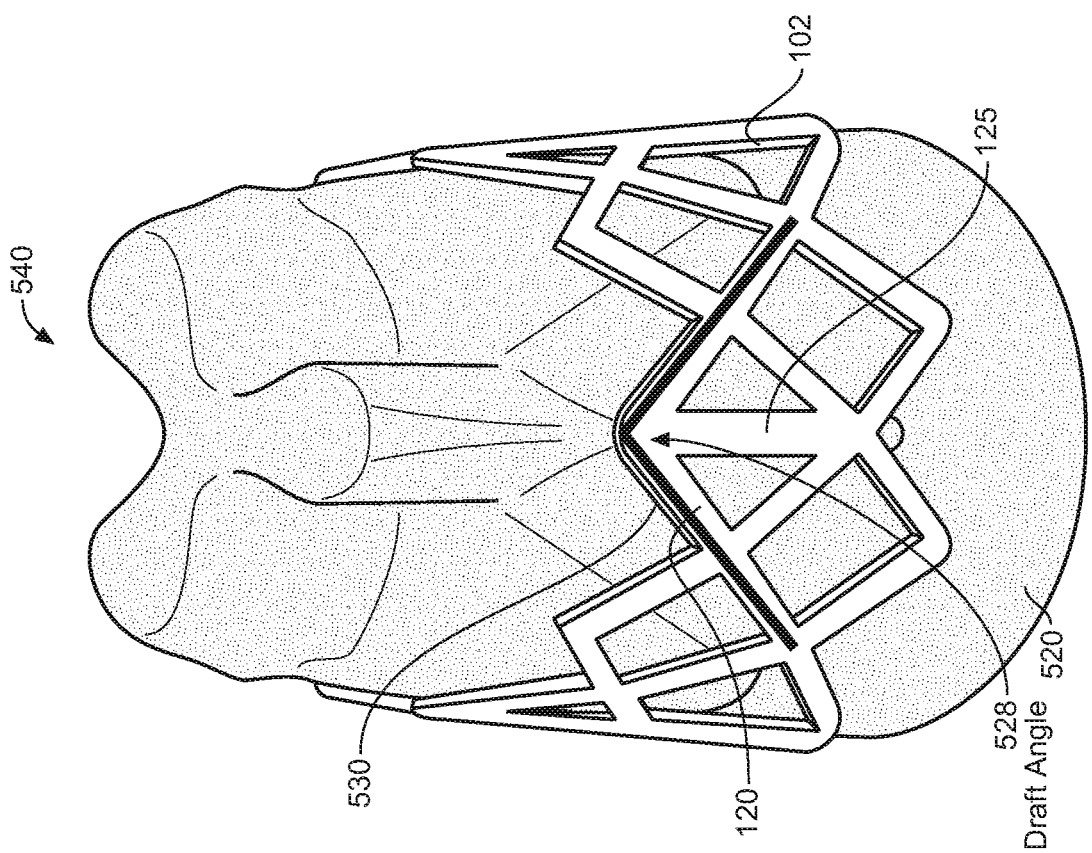
FIGS. 5B-5C are perspective views of an example embodiment of a mold before and after placement of an example stent thereon, respectively.
Figure 5B:
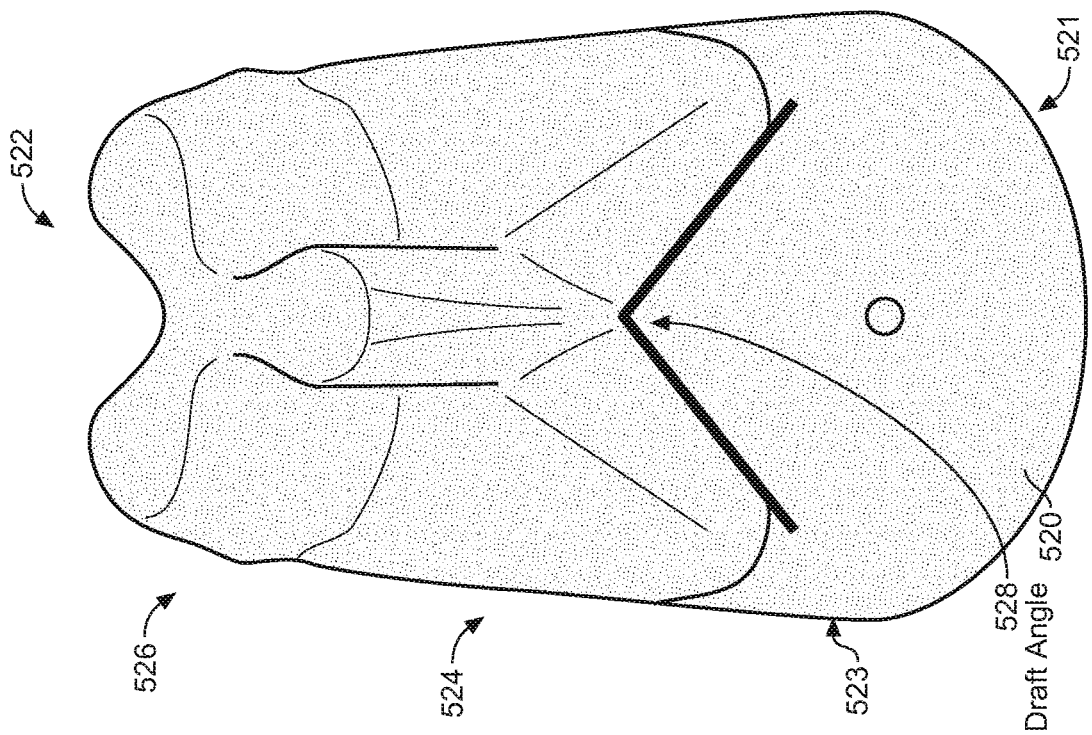

FIG. 5B is a perspective view depicting mold 520 and FIG. 5C is a perspective view depicting mold 520 after coupling with stent 102, resulting in a mold and stent assembly 540. In the context of dipping and curing, the terms "upward" (e.g., "facing upward") and "downward" (e.g., "facing downward") are used in their normal sense with respect to the force of gravity. Thus in FIGS. 5B and 5C, upstream end 521 of mold 520 is facing downward and downstream end 522 is facing upward.

For dipping, in this embodiment, mold 520 is turned upside down from the orientation depicted here, such that upstream end 521 of mold 520 is above downstream end 522 (upstream end 521 is facing upward and downstream end 522 is facing downward). Mold 520 includes a base portion 523 with a geometry configured to form to upstream portion of valvular body 104. Mold 520 also includes a leaflet portion 524 with a surface that forms a negative image of the interior geometry of leaflets 110 in a partially open at-rest position. Above leaflet portion 524 is a run-off portion 526 that allows excess polymer to run-off or drain away from leaflets 110 after dipping, if the curing process takes place with downstream end 522 of mold facing downward (in some embodiments, curing can take place while downstream end 522 faces upward). The polymer that cures on run-off portion 526 can be removed during leaflet finishing where, e.g., leaflets 110 are trimmed to their final dimensions. In some embodiments, the trimming step can involve removal of run-off portion 526 itself from mold 520.

In this embodiment, stent 102 is placed on mold 520 such that the three draft angles 528 (located between each pair of adjacent leaflets on mold 520) are aligned with the proper respective positions on stent 102, which can be positions corresponding to commissure positions where adjacent leaflets meet (e.g., positions 111 of FIG. 1B). In this embodiment, these positions are downstream termini of three crown segments 530. Placement can be such that struts 120 forming crown segments 530 coincide with the draft angle 528, as shown in FIG. 5C. Alignment of struts 120 with draft angle 528 allows even distribution of stress to stent 102, and also allows the struts of each crown segment 530 aligned with draft angle 528 to deflect radially inward during operation of valve 100. This deflection can absorb strain energy resulting from the closing of valve leaflets 110 that would otherwise result in strain on leaflet 110 itself. Furthermore this deflection increases the likelihood of clearance of all aortic sinuses even if valve 100 is misaligned when implanted.

Coupling stent 102 to mold 520 while stent 102 is wet allows stent 102 to adhere to mold 520 at thus remain in the proper position during the dipping process, and also allows the subsequently applied polymer to cure with a stronger bond to stent 102. At 506, mold and stent assembly 540 can be dipped into wet polymer such that run-off portion 526 is submerged first. In this and all embodiments described herein, mold 520 can be submerged until at least leaflet portion 524 of mold 520 is covered. The extent to which base portion 523 is submerged can vary. For example, if valvular body 104 is configured with a skirt 140, then submergence of mold 520 should continue at least far enough to form skirt 140. Mold 520 can be submerged past the desired upstream terminus of skirt 140 and any excess polymer can be trimmed to form skirt 140.

This dipping at 506 preferably occurs with the same polymer as used at 502, although a different batch may be used. In some embodiments, the polymer used in 506 may have a different viscosity or chemical composition from the polymer used at 502. Although the methods disclosed herein are not limited to such, in some example embodiments, the dipping steps (in this and all embodiments described herein) can occur under both high temperature and humidity, for example with a relative humidity (RH) in the range of 20-80% and a temperature in the range of 20-50 degrees C. Furthermore, each dipping step (in this and all embodiments described herein) can occur with one submergence or multiple submergences of the mold and/or stent.

At 508, assembly 540 is allowed to cure such that downstream end 522 is facing downward and the polymer can drain along run-off portion 526. The curing recipe will vary depending on the type of polymer used. After curing, stent 102 and valvular body 104 will be securely fixed together to form valve 100.

In this and all embodiments herein, valve 100 can be complete after curing, or valve 100 can be subjected to valve finishing to finalize the valve structure. Examples of finishing can include trimming or modifying the surface of leaflets 110 to their final or near final state (e.g., through laser cutting, ultrasonic trimming, water knife, a mechanical clam shell cutter, and the like), applying additional coatings or surface treatments to valve 100, moving skirt 140 (e.g., rolling skirt 140 over stent 102), attaching additional structures to valve 100 (such as bands or tensioning elements as described herein), or others. Packaging and sterilization of the finished valve can then occur.

In this embodiment, trimming of leaflets 110 can occur once leaflets 110 are cured. In this and all other embodiments described herein, trimming of leaflets 110 can occur once leaflets 110 are cured, regardless of whether additional manufacturing steps (e.g., mating of valvular body 104 with stent 102) are still to be performed.

Figure 4D:
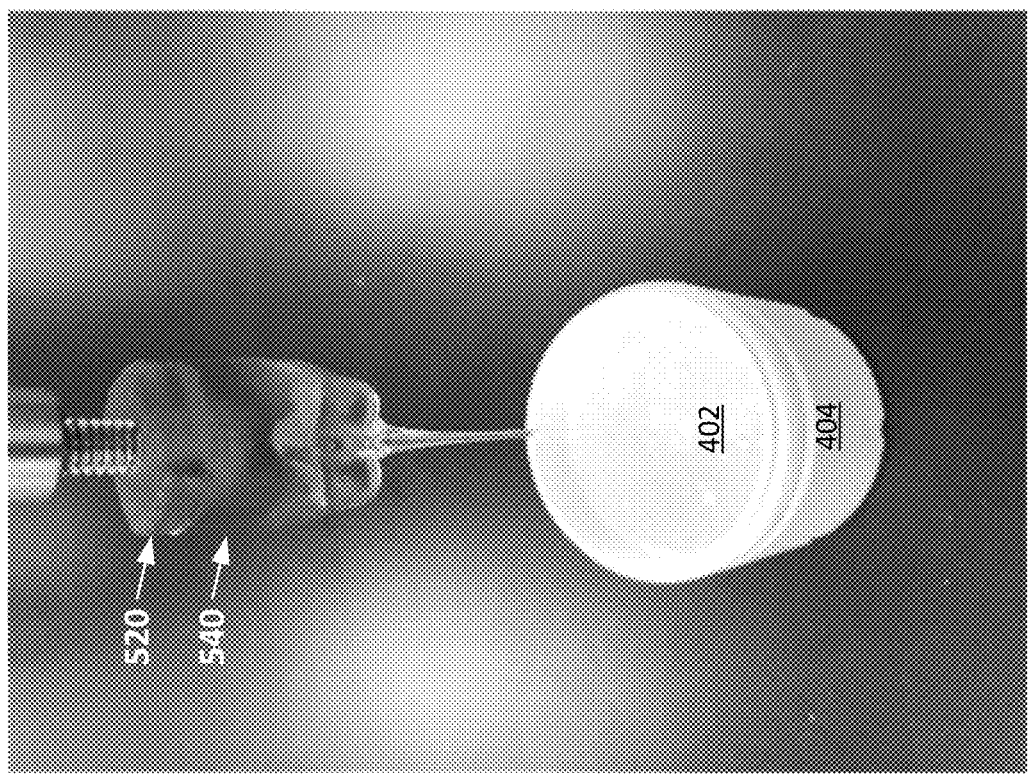
Figure 4C:
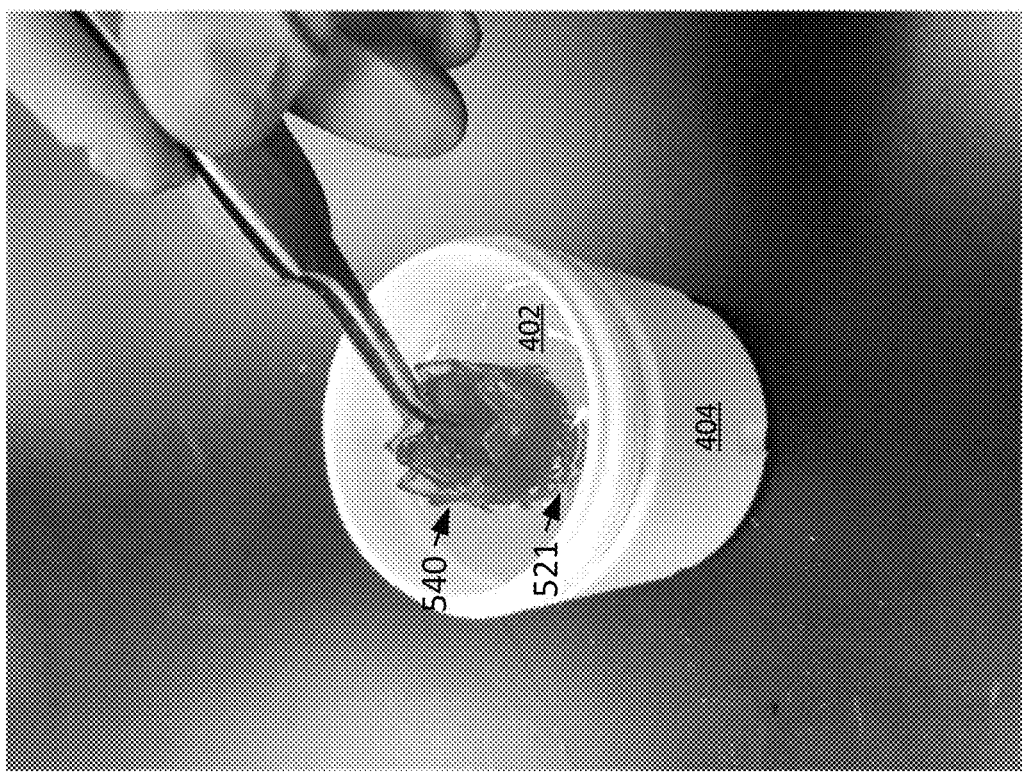
Figure 4F:
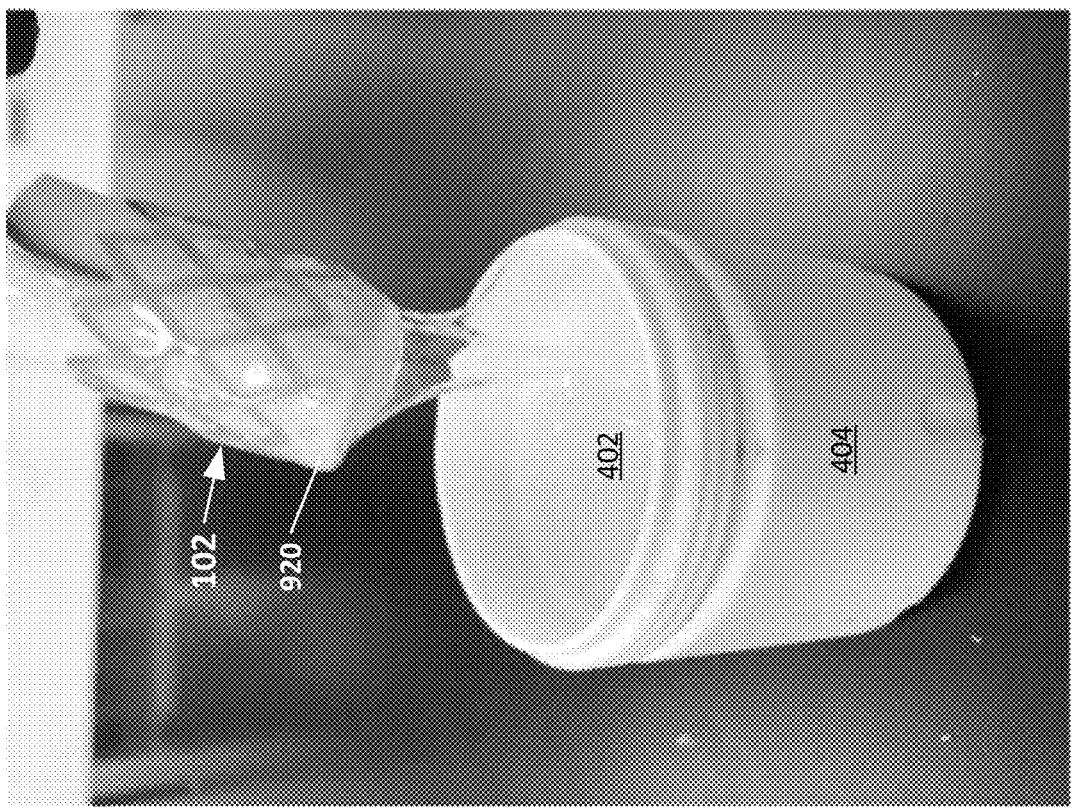
Figure 4E:
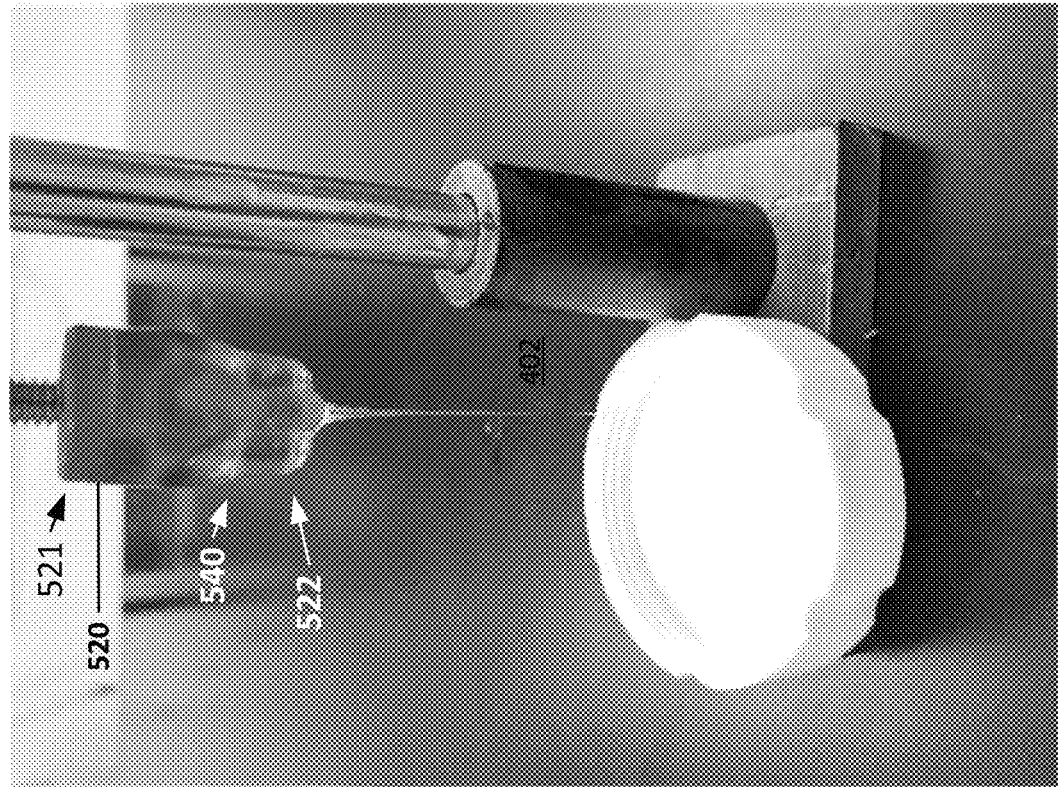
Figure 6A:
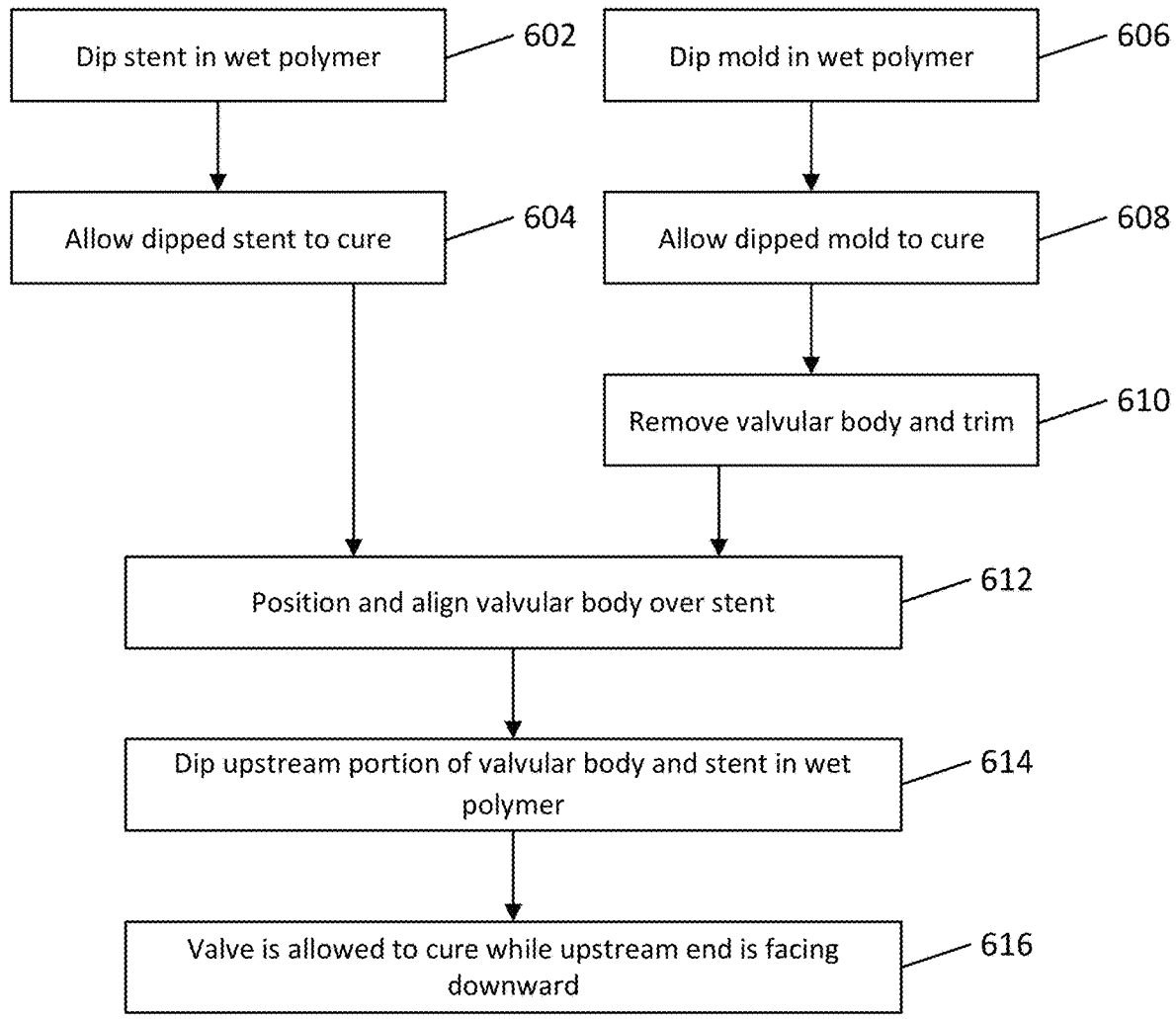
FIG. 6A is a flow diagram depicting an example embodiment of a method of manufacturing a valve.
Figure 6B:
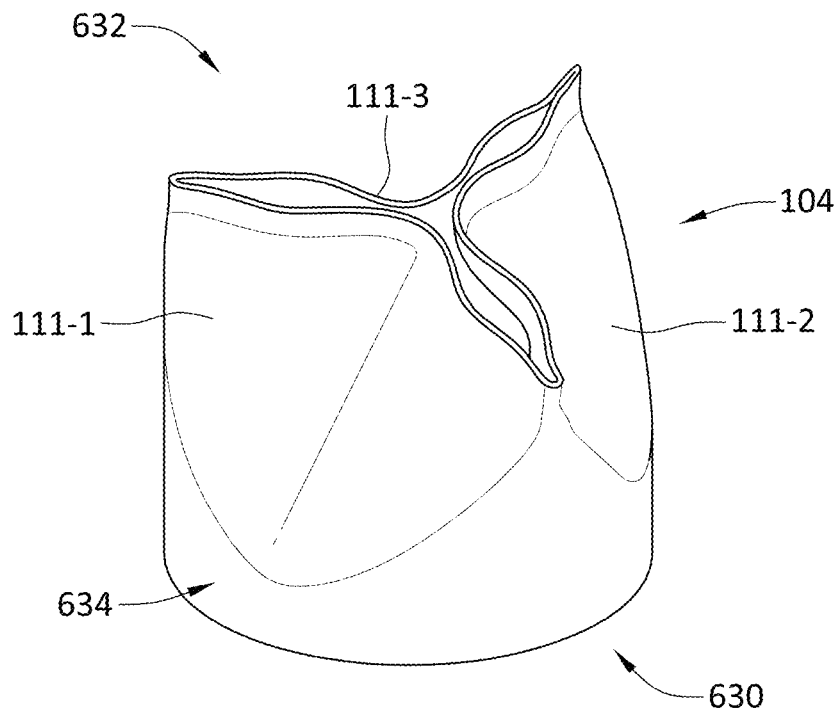
FIGS. 6B-6C are perspective and top down views, respectively, of an example embodiment of a stent of a valvular body in an expanded state.
Figure 6C:
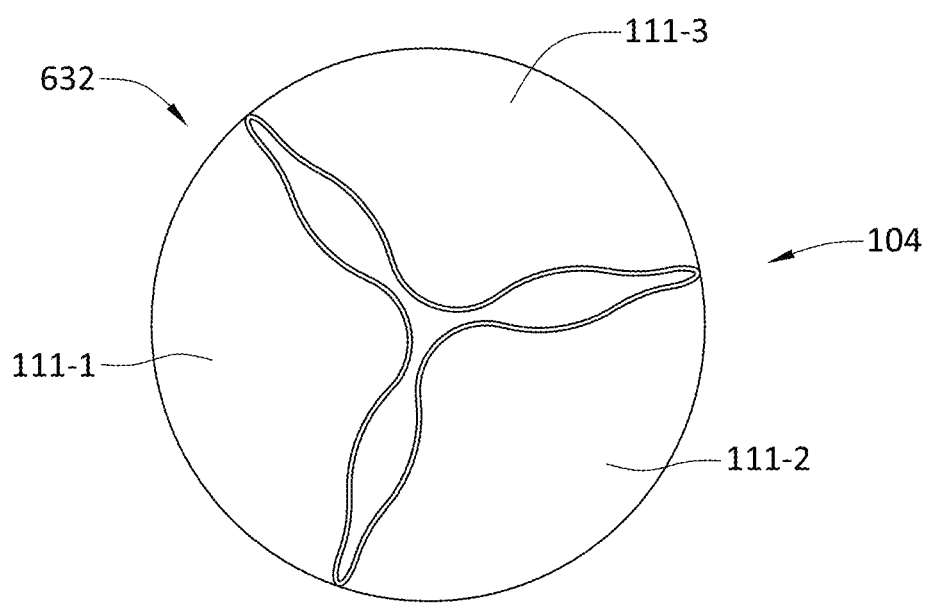

FIG. 6A is a flow diagram depicting another example embodiment of a method 600 of manufacturing valve 100. At 602 stent 102 is dipped in wet polymer such that at least a portion, preferably all, of the stent body is encapsulated in polymer (FIG. 4A). Then at 604 stent 102 is allowed to completely cure to a dry state or substantially cure to a substantially dry state. Coating of stent 102 can be performed as part of method 600 or stent 102 can be precoated, or the coating can be omitted. Separately, valvular body 104 is formed. This can occur at 606-610. At 606 mold 520 is dipped such that the downstream end 522 is submerged first and continued until leaflet portion 524 and optionally at least a portion of base portion 523 is submerged, after which mold 520 is removed (FIG. 4D). At 608 mold 520 is also allowed to completely cure to a dry state or substantially completely cure to a substantially dry state to form valvular body 104 (FIG. 4E). FIGS. 6B and 6C are perspective and top down views of an example embodiment of valvular body 104 (having upstream end 630 and downstream end 632) after removal from mold 520.

Figure 6D:
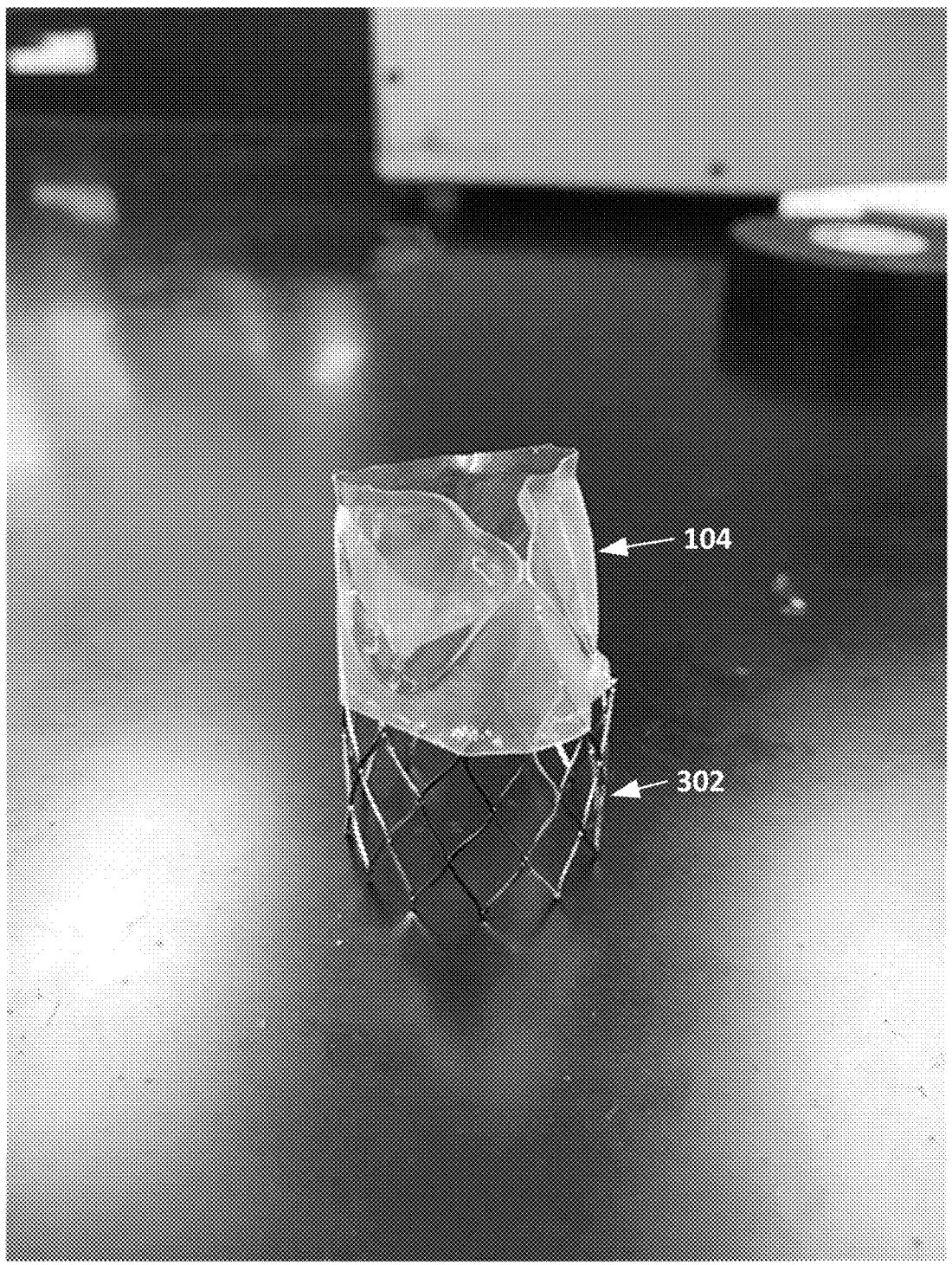
FIG. 6D is a photograph depicting an example stage of manufacturing an example embodiment of a valve.

At 610 the resulting valvular body 104 is removed from mold 520 and leaflets 110 can be trimmed, in either order. At 612 valvular body 104 is then positioned over stent 102 and aligned. FIG. 6D is a photograph of an example embodiment of valvular body 104 partially positioned over a stent, in this instance stent 302. At 614 the valvular body and stent assembly is then dipped in polymer such that the upstream end is submerged first, preferably over an upstream portion 634 of valvular body 104 (FIG. 6B), but preferably stopping short of leaflets 110, to attach valvular body 104 to stent 102. This can be accomplished by grasping a portion of the assembly that is not to be dipped (e.g., leaflets 110 and/or a downstream portion of stent 102) and then dipping the assembly into the polymer. At 616 valve 100 is then allowed to cure while upstream end 106 is facing downward. Then valve 100 can be finished as needed, including any necessary trimming to upstream end 106 and rolling or inverting skirt 140 over stent 120 (FIG. 2C) if desired.

Figure 7:
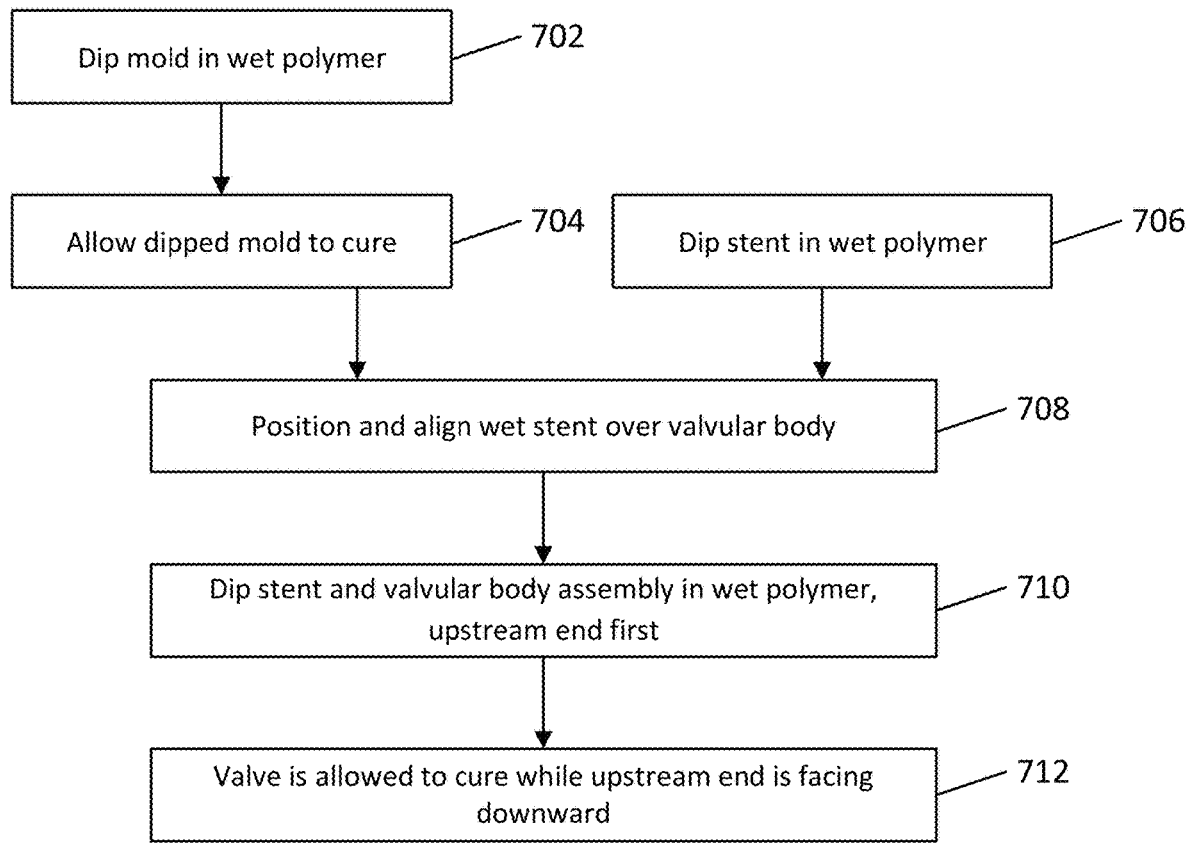

FIG. 7 is a flow diagram depicting another example embodiment of a method 700 of manufacturing valve 100. Valvular body can be formed, e.g., at 702-704. At 702, mold 520 is dipped into wet polymer such that downstream end 522 is submerged first and continued until leaflet portion 524 and optionally at least a portion of base portion 523 is submerged, after which mold 520 is removed (FIG. 4D). At 704 mold 520 is then hung with downstream end 522 beneath upstream end 520 (such that excess polymer runs off run-off portion 526) and the polymer is allowed to completely cure to a dry state or substantially completely cure to a substantially dry state to form valvular body 104 (FIG. 4E). After valvular body 104 is cured, at 706 stent 102 is dipped in order to at least partially, and preferably entirely, encapsulate stent 102 in polymer. At 708 stent 102, while in a wet state, is positioned over valvular body 104 and mold 520 and properly aligned as needed (see FIG. 4B). At 710 assembly 540 is then dipped again such that upstream end 521 is submerged first (see FIG. 4C). Assembly 540 is dipped to cover an upstream portion of valvular body 104 (like portion 634 of FIG. 6B), but preferably stopping short of leaflets 110. The dipping at 710 can form skirt 140. At 712 valvular body 104 and stent 102 are allowed to cure with upstream end 106 facing downward, to attach the two together and form valve 100. Valve 100 can then be finished as needed, including any necessary trimming to upstream end 106 and rolling or inverting skirt 140 over stent 120 (FIG. 2C) if desired.

Figure 8:
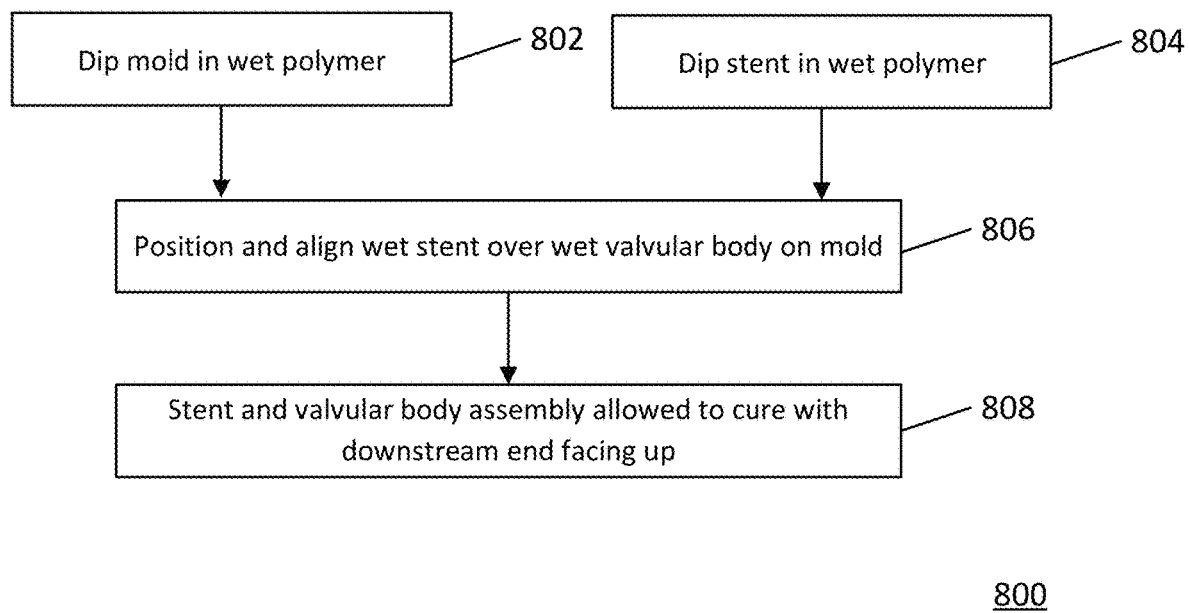

FIG. 8 is a flow diagram depicting another example embodiment of a method 800 of manufacturing valve 100. At 802, mold 520 is dipped into wet polymer such that downstream end 522 is submerged first, leaflet portion 524 is covered, and optionally at least a portion of base portion 523 is covered. At 804, stent 102 is dipped in order to at least partially, and preferably entirely, encapsulate stent 102 in polymer. 802 and 804 can be performed in any order or concurrently. At 806, after dipping stent 102 and mold 520 and while both are still in an at least partially wet state (e.g., immediately after dipping, or after one or both of stent 102 and body 104 have partially cured), stent 102 is positioned over body 104 on mold 520 and aligned as needed. At 808, the assembly is allowed to cure with downstream end 108 facing up. Curing the assembly while in this orientation utilizes gravity to create skirt 140 out of excess polymer running over base portion 523 of mold 520. This excess polymer would otherwise drip off run-off portion 526 of mold 520. Valve 100 can then be removed from mold 520 and finished as needed, including any necessary trimming to upstream end 106 and rolling or inverting skirt 140 over stent 120 (FIG. 2C) if desired.

Figure 9:
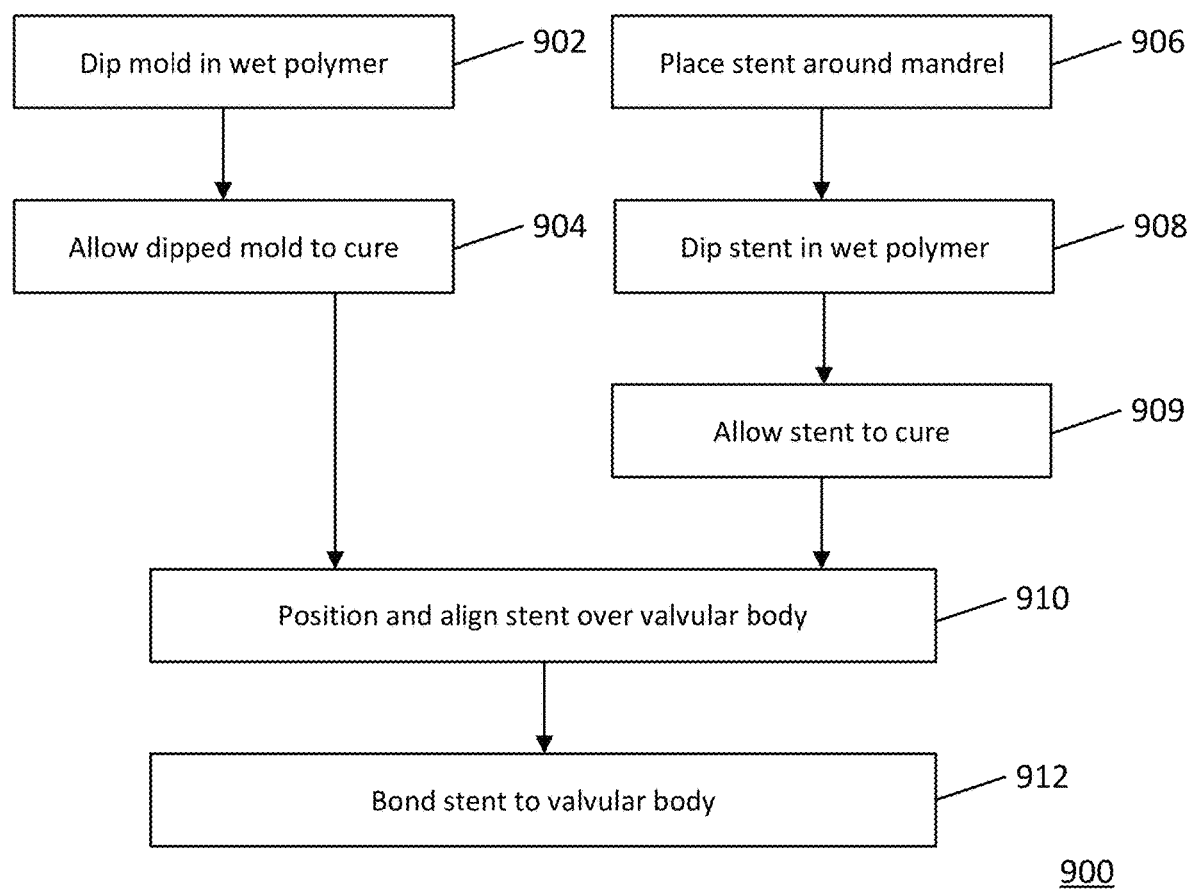

FIG. 9 is a flow diagram depicting another example embodiment of a method 900 of manufacturing valve 100. At 902, mold 520 is dipped into wet polymer such that downstream end 522 is submerged first, leaflet portion 524 is covered, and optionally at least a portion of base portion 523 is covered. At 904, mold 520 is then hung with downstream end 522 beneath upstream end 521 (such that excess polymer runs off run-off portion 526) and the polymer is allowed to completely cure to a dry state or substantially completely cure to a substantially dry state to form valvular body 104 (FIG. 4E). At 906, stent 102 is fixed around a mandrel (e.g., a cylindrical mandrel). At 908, stent 102 and the mandrel are dipped in order to at least partially, and preferably entirely, encapsulate stent 102 in polymer (see FIG. 4F). Use of the mandrel assists in forming a uniform and repeatable inner diameter to the stent body as well as establishing skirt 140. At 909, stent 102 is allowed to cure. At 910, after valvular body 104 and stent 102 are cured, stent 102 is placed over valvular body 104 (e.g., while still on mold 520) and stent 102 is bonded to body 104. If desired, skirt 140 can be rolled or inverted over stent 120 (FIG. 2C) prior to bonding. Many types of bonding methods can be used, and the chosen method is preferably tailored to the polymer composition(s). Examples of bonding methods include, but are not limited to, polymeric bonding, solvent bonding, plasma bonding, and ultrasonic welding. Valve 100 can then be finished as needed.

Figure 10A:
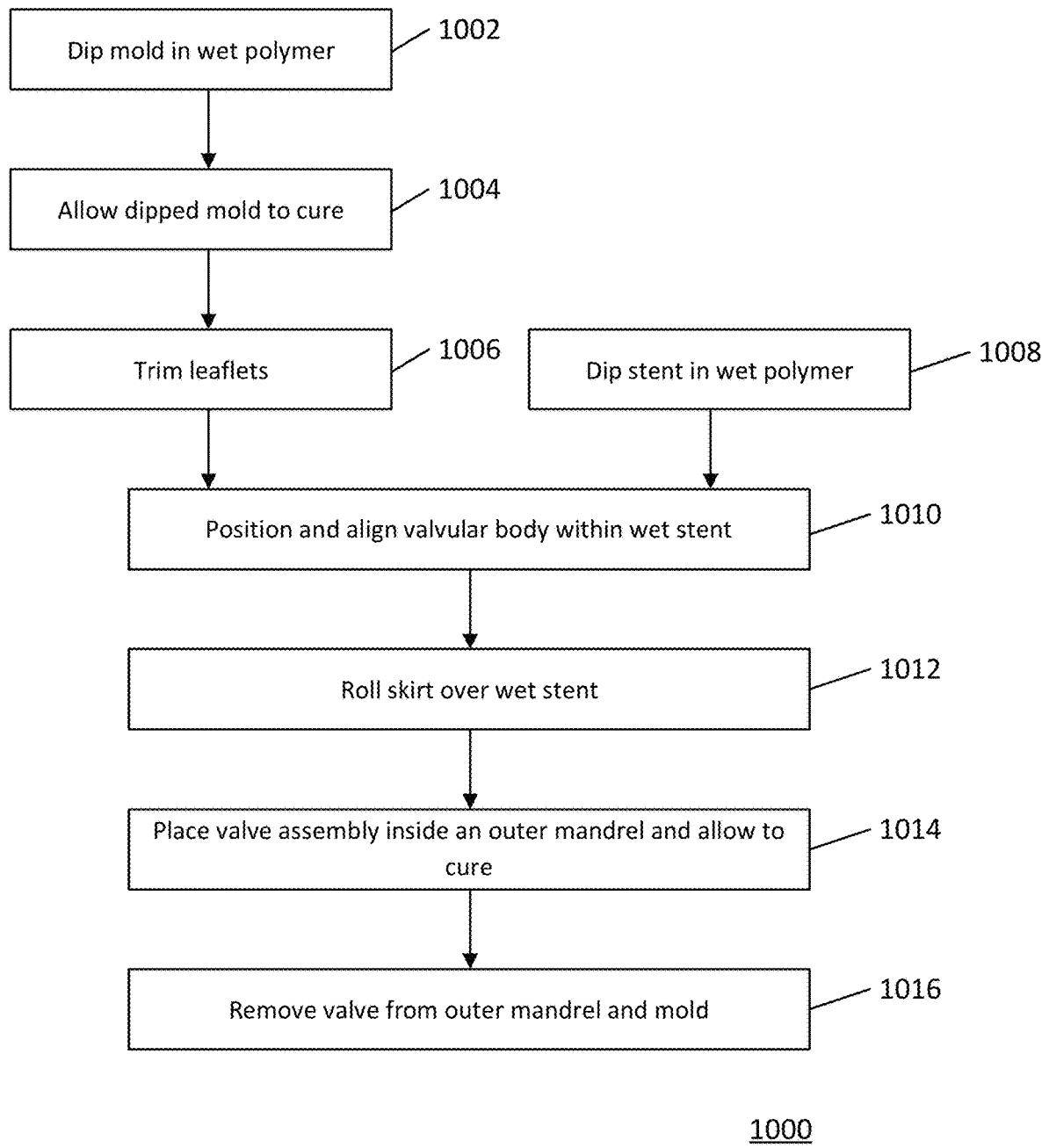

FIG. 10A is a flow diagram depicting another example embodiment of a method 1000 for manufacturing valve 100. At 1002, mold 520 is dipped into wet polymer such that downstream end 522 is submerged first, leaflet portion 524 is covered, and optionally at least a portion of base portion 523 is covered. At 1004, mold 520 is then hung with downstream end 522 beneath upstream end 520 (such that excess polymer runs off run-off portion 526) and the polymer is allowed to completely cure to a dry state or substantially completely cure to a substantially dry state to form valvular body 104 (FIG. 4E). At 1006, leaflets 110 can optionally be trimmed and/or otherwise finished while valvular body 104 is on mold 520. At 1008, stent 102 is dipped in order to at least partially, and preferably entirely, encapsulate stent 102 in polymer. At 1010, while stent 102 is still wet, valvular body 104 is placed inside stent 102, preferably while valvular body 104 is still on mold 520, and aligned with stent 102. At 1012, if a skirt 140 is present in valvular body 104, skirt 140 can be rolled, inverted, or otherwise placed over the upstream side of stent 102 (see FIG. 2C).

Figure 10B:
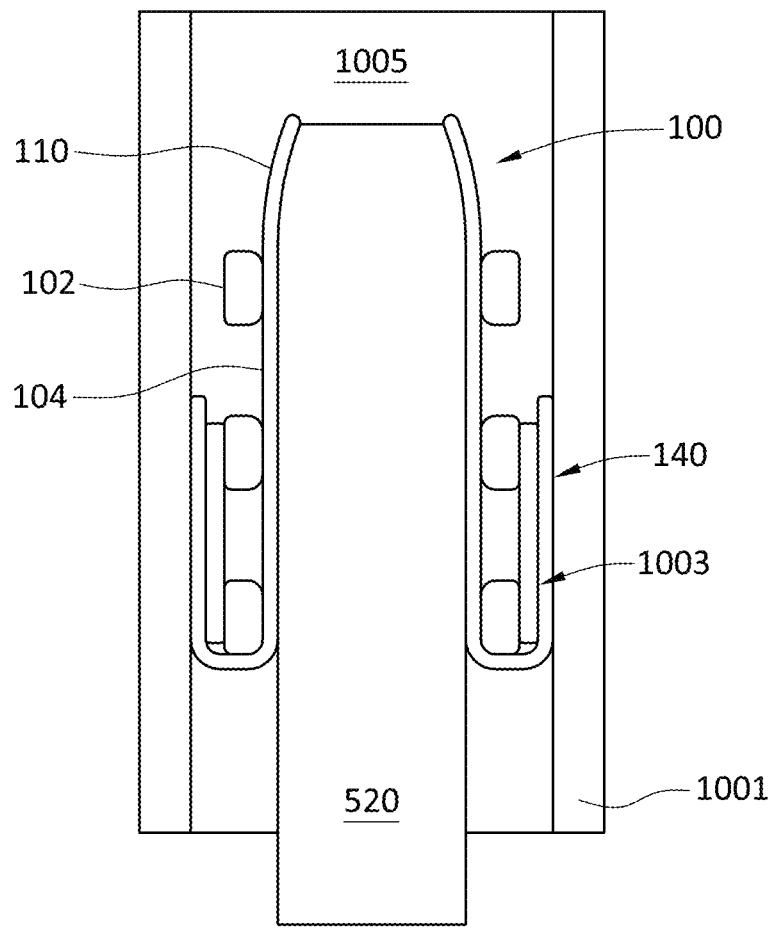
FIG. 10B is a cross-sectional view depicting an example embodiment of a valve during manufacturing.

At 1014, the valve assembly can be placed inside a lumen or recess of an outer mold or mandrel and allowed to cure. FIG. 10B is a cross-sectional view of mold 520 having valvular body 104 thereon (after trimming of leaflets 110 and removal of run-off portion 526). Stent 102 is over valvular body 104 and skirt 140 has been rolled over stent 102. The assembly is within an interior space 1005 of outer mandrel 1001. An optional tubular debonding shim 1003 can be placed between the exterior of stent 102 and the interior of skirt 140 to prevent adhesion of the two. Outer mandrel 1001 exerts force on valve 100 to assist in curing stent 102 to valvular body 104 and forming sufficient securement of the two elements together. At 1016 valve 100 can be removed from outer mandrel 1001 and mold 520. Before or after removal from mold 520, any debonding shim 1003 can be removed from valve 100 and, also, an optional band or other tensioning element (e.g., pre-stretched) can be placed around skirt 140 to hold skirt 140 in place around stent 102 if desired. The tensioning element can be hydrophilic such that it swells within the body, which can assist in the prevention of paravalvular leakage. Valve 100 can then be finished as needed.

Figure 11:
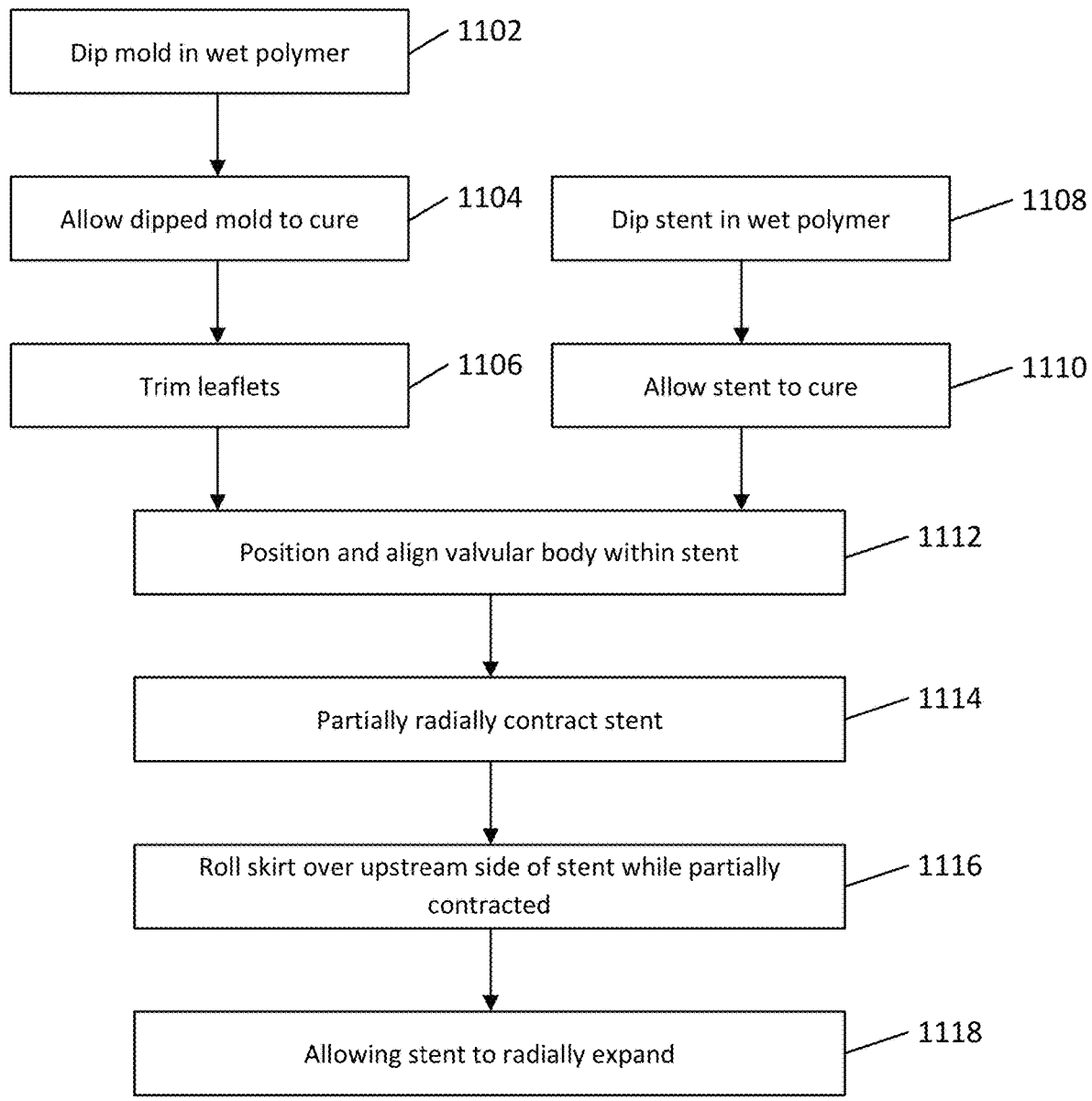

FIG. 11 is a flow diagram depicting another example embodiment of a method 1100 for manufacturing valve 100. At 1102, mold 520 is dipped into wet polymer such that downstream end 522 is submerged first, leaflet portion 524 is covered, and optionally at least a portion of base portion 523 is covered. At 1104, mold 520 is then hung with downstream end 522 beneath upstream end 520 (such that excess polymer runs off run-off portion 526) and the polymer is allowed to completely cure to a dry state or substantially completely cure to a substantially dry state to form valvular body 104 (FIG. 4E). At 1106, leaflets 110 can optionally be trimmed and/or otherwise finished while valvular body 104 is on mold 520. At 1108, stent 102 is optionally dipped in polymer in order to at least partially, and preferably entirely, encapsulate stent 102 in polymer. At 1110, stent 102 (if dipped) can be allowed to cure to a dry state.

At 1112, valvular body 104 can be placed inside and aligned with stent 102, preferably after valvular body 104 has been removed from mold 520. In this embodiment, 1112 is performed while stent 102 is dry, but in other embodiments stent 102 can be in a wet state after dipping in wet polymer. At 1114, stent 102 is partially contracted or crimped towards its contracted configuration using outer mandrel 1001 or another crimping device. At 1116, while in the partially contracted state, skirt 140 can be rolled, inverted, or otherwise placed over the upstream side of stent 102. Skirt 104 is preferably of a radial dimension that is less than the fully self-expanded radial dimension of stent 102, and thus stent 102 and valvular body 104 are held together by the expansive force applied by stent 102 against the interior of skirt 140. At 1118, stent 102 can be allowed to radially expand back to its expanded state, or until the resistance applied by skirt 140 impedes further expansion. This can be accomplished by removing stent 102 from outer mandrel 1001. An optional band or other tensioning element (e.g., pre-stretched) can be placed around skirt 140 to add further securement. Again, the tensioning element can be hydrophilic such that it swells within the body, which can assist in the prevention of paravalvular leakage. Valve 100 can then be finished as needed.

Figure 12:
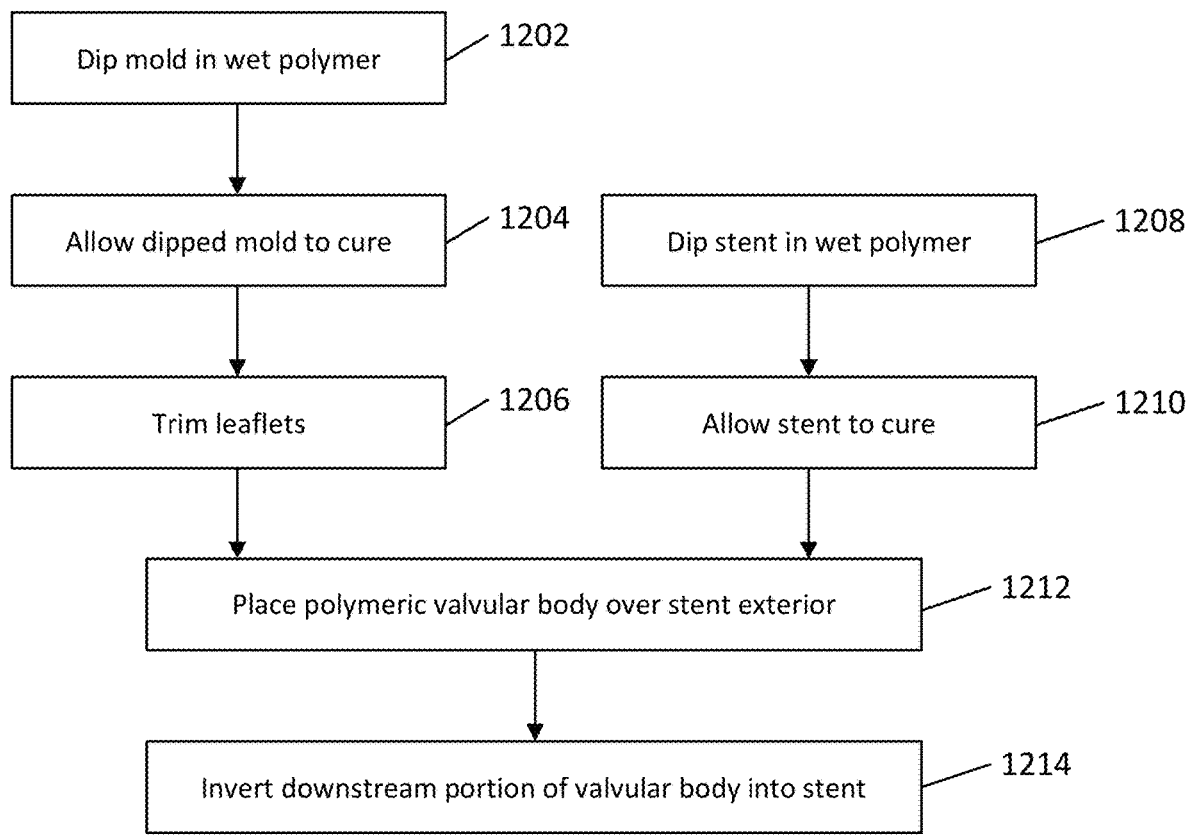

FIG. 12 is a flow diagram depicting another example embodiment of a method 1200 for manufacturing valve 100. At 1202, mold 520 is dipped into wet polymer such that downstream end 522 is submerged first, leaflet portion 524 is covered, and optionally at least a portion of base portion 523 is covered. At 1204, mold 520 is then hung with downstream end 522 beneath upstream end 520 (such that excess polymer runs off run-off portion 526) and the polymer is allowed to completely cure to a dry state or substantially completely cure to a substantially dry state to form valvular body 104 (FIG. 4E). At 1206, leaflets 110 can optionally be trimmed and/or otherwise finished while valvular body 104 is on mold 520. At 1208, stent 102 is optionally dipped in order to at least partially, and preferably entirely, encapsulate stent 102 in polymer. At 1210, if dipped, then stent 102 can be allowed to cure.

Valvular body 104 can then be removed from mold 520 and, at 1212, at least a portion of skirt 140 on an upstream side of valvular body 104 can be placed over a portion of the exterior of stent 102. In doing so, leaflets 110 of valvular body 104 are aligned with stent 102, e.g., with struts or crown segments on stent 102 configured for alignment with commissure locations between leaflets 110. At 1214, the downstream end or side of valvular body 104 is inverted or rolled into the interior (inner lumen) of stent 102 such that leaflets 110 are positioned in the within stent 102 in a manner that permits leaflets to operate to regulate the flow of blood. An optional band or other tensioning element (e.g., pre-stretched) can then be placed around skirt 140 to add further securement. Again, the tensioning element can be hydrophilic such that it swells within the body, which can assist in the prevention of paravalvular leakage. Valve 100 can then be finished as needed.

Figure 13A:
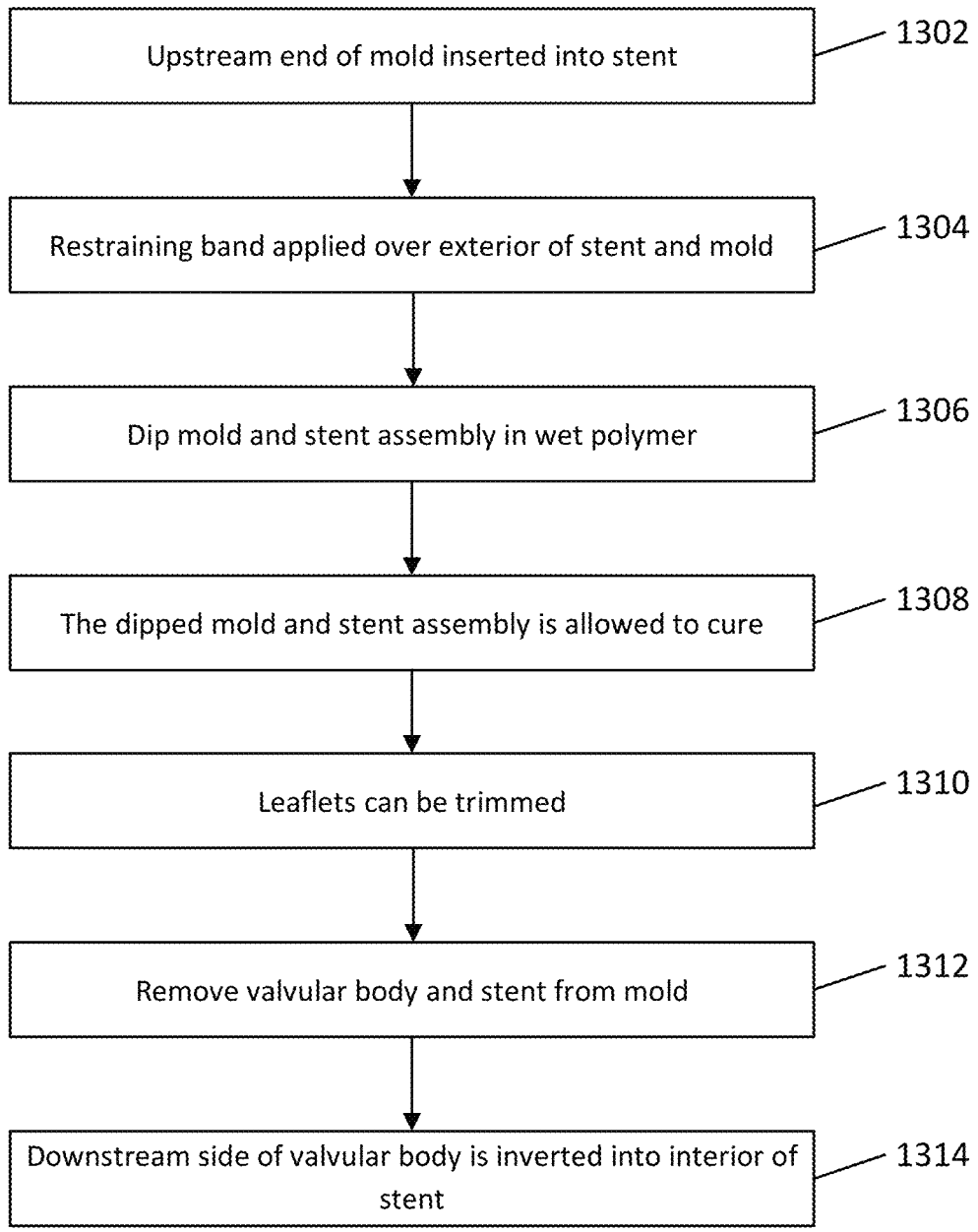
Figure 13B:
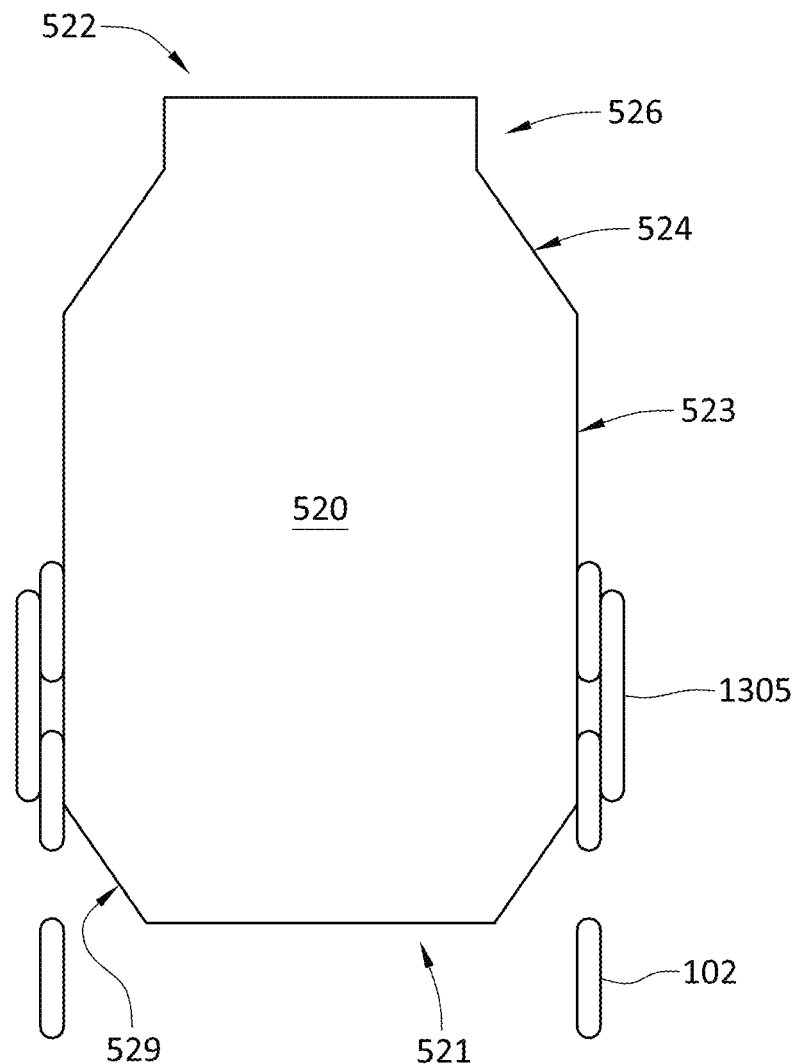
FIG. 13B is a cross-sectional view depicting an example embodiment of a valve during manufacturing.

FIG. 13A is a flow diagram depicting another example embodiment of a method 1300 for manufacturing valve 100. At 1302, upstream end 521 of mold 520 is inserted into stent 102 (which can be previously dipped and cured if desired) such that at least a portion of stent 102 is over on base portion 523 of mold 520, but not extending over leaflet portion 524 of mold 520 (e.g., not as far as depicted in FIG. 5C). Upstream end 521 of mold 520 can include a taper to assist in insertion if desired. At 1304, a round band or other tensioning element can optionally be placed over the exterior of stent 102 to hold it to mold 520. FIG. 13B is a cross-sectional view depicting an example of such an arrangement with band 1305 placed over stent 102. As depicted here, upstream end 521 of mold 520 includes a tapered portion 529.

At 1306, mold 520 is dipped into wet polymer such that downstream end 522 is submerged first, leaflet portion 524 is covered, and a portion of base portion 523 is covered, preferably up to or near to the upstream terminus of band 1305. At 1308, mold 520 is then hung with downstream end 522 beneath upstream end 520 (such that excess polymer runs off run-off portion 526) and the polymer is allowed to completely cure to a dry state or substantially completely cure to a substantially dry state to form valvular body 104.

At 1310, leaflets 110 can optionally be trimmed and/or otherwise finished while valvular body 104 is on mold 520. At 1312, valvular body 104 and stent 102, which are held together by the cured polymer, are removed from mold 520. At 1314, the downstream side of valvular body 104 is inverted into the interior of stent 102 to place leaflets 110 at the desired position within stent 102. An additional exterior band or tensioning element (e.g., hydrophilic) can be applied around the exterior of valve 100, if desired. Valve 100 can then be finished as needed.

Mold 520, in all of the embodiments described herein, can be configured such that leaflet forming portion 524 does not include an image of leaflets 110 but rather has a cylindrical or substantially cylindrical shape, as is known to those of ordinary skill in the art. Such a shape will result in a cylindrical or substantially cylindrical portion of valvular body 104 where leaflets 110 are to be positioned, and those leaflets 110 can then be formed by trimming and/or shaping valvular body 104 accordingly.

In addition to the securement techniques already mentioned, in all of the embodiments described herein, the commissure of valvular body 104 between adjacent leaflets 110 can be bonded, sewn, or otherwise secured to stent 102 thru additional methods to provide additional support at that location.

In all of the embodiments of valve 100 described herein, one or more anchors, barbs, abutments, or other structures that extend radially outwards from valve 100 can be positioned on stent 102 and/or valvular body 104, such as near upstream end 106. Such elements can act as fasteners that assist in lodging valve 100 to the surrounding tissue after implantation.

In all of the embodiments described herein, mold 520 and/or mandrel 1001 can be a material (or be coated with a material) that resists cohesion with the polymer(s) used. Such a configuration can make it easier to remove valvular body 104 and/or stent 102 from mold 520 and/or mandrel 1001.

In all of the embodiments described herein, polymers having different characteristics can be used. These characteristics can include viscosity, chemical composition, the presence of additives, and the like. For example, mold 520 and stent 102 can each be dipped in a polymer having the same characteristics, or different characteristics. If mold 520 and/or stent 102 is dipped multiple times in an embodiment, then each dipping can be with a polymer having the same or a different characteristic.

The embodiments of valve 100 described herein are trileaflet (three leaflet) valves, although valve 100 can be implemented and manufactured as a bileaflet (two leaflet) valve in the alternative. Upon review of the present document, those of ordinary skill in the art will readily recognize how to implement and manufacture valve 100 as a bileaflet valve without requiring such to be shown in a figure.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In many example embodiments, an implantable valve is provided that includes: a stent including a plurality of deflectable struts; and a polymeric valvular body coupled with the stent, the polymeric valve body including a plurality of artificial leaflets, where the implantable valve has a radial dimension and is transitionable between a contracted state and an expanded state, where the radial dimension is relatively smaller in the contracted state than in the expanded state.

In these valve embodiments, the stent and valvular body can be coupled together with cured polymer. The stent can be encapsulated in the cured polymer. The polymeric valvular body can be composed of the cured polymer.

In these valve embodiments, the implantable valve can have a longitudinal axis and, when the implantable valve is in the expanded state, the plurality of deflectable struts are transverse to the longitudinal axis. When in a fully contracted state, the plurality of deflectable struts can be parallel or substantially parallel to the longitudinal axis. The valve can further include a plurality of longitudinal struts, each of the plurality of longitudinal struts positioned at a commissure between adjacent leaflets. Each of the plurality of longitudinal struts can be parallel to a longitudinal axis of the implantable valve when the implantable valve is in the expanded and contracted configurations. The plurality of deflectable struts can cross and form a plurality of cells. The stent can include a first row of cells located adjacent a downstream end of the stent, where the plurality of longitudinal struts are in the first row of cells. The stent can include a second row of cells located upstream of the first row of cells, where no longitudinal strut is in the second row of cells.

In these valve embodiments, the valvular body can include a skirt located upstream from an upstream end of the stent. The skirt can extend over the upstream end of the stent. The skirt can extend over an exterior upstream portion of the stent. The skirt can extend over the exterior upstream portion of the stent and can be unconnected (not bonded) to the exterior upstream portion of the stent.

In these valve embodiments, the stent can include a primary crown and a secondary crown. The primary crown can include a plurality of primary crown segments and the secondary crown can include a plurality of secondary crown segments. A downstream terminus of each of the plurality of primary crown segments can be radially aligned with an interface between adjacent leaflets. Each of the plurality of secondary crown segments can have a downstream terminus that is upstream of the downstream terminus of each of the plurality of primary crown segments. The stent can include a waist, and where the primary and secondary crowns extend radially outwards relatively farther than the waist when the implantable valve is in the expanded configuration. The secondary crown can extend radially outwards relatively farther than the primary crown when the implantable valve is in the expanded configuration. The secondary crown can be configured to deflect from a first position radially outwards when the valve opens and deflect back to the first position when the valve closes. The stent can include a tertiary crown located upstream of the primary and secondary crowns. The tertiary crown can include a plurality of tertiary crown segments. An upstream terminus of the stent can be formed by an upstream terminus of each of the plurality of tertiary crown segments. The stent can include a waist, and the primary crown, secondary crown, and tertiary crown can extend radially outwards relatively farther than the waist when the implantable valve is in the expanded configuration. The secondary crown can extend radially outwards relatively farther than the primary crown and the tertiary crown when the implantable valve is in the expanded configuration.

In these valve embodiments, the plurality of leaflets can be two and only two leaflets, or the plurality of leaflets can be three and only three leaflets. Other numbers of leaflets can also be used. In these valve embodiments, the implantable valve can be configured to replace an aortic valve of a human heart. In these valve embodiments, the implantable valve can be configured to replace a mitral valve of a human heart. In these valve embodiments, the stent can include a primary structure with a secondary structure coated over the primary structure.

In many example embodiments, methods of implanting a prosthetic valve are provided, where the methods include: moving the prosthetic valve, with an elongate delivery device while the prosthetic valve is in a contracted state, through a body of a recipient; and implanting the prosthetic valve in the body of the recipient by, at least, deploying the prosthetic valve from the delivery device, where the prosthetic valve is implanted in an expanded configuration, and where the prosthetic valve is in accordance with any of the aforementioned valve embodiments.

In many example embodiments, first methods of manufacturing an implantable valve are provided, where the first methods include: dipping a stent in wet polymer; placing the stent on a mold; dipping the mold and stent into wet polymer such that at least a portion of the mold and at least a portion of the stent are covered in a polymer coating; and allowing the polymer coating to cure.

In these example embodiments of first methods, the mold can include a contoured surface to form leaflets. The stent can be placed on the mold such that the stent is aligned with the contoured surface on the mold. The contoured surface of the mold has a draft angle that is aligned with a commissure position on the stent.

These example embodiments of first methods can include trimming the polymer coating to form a plurality of leaflets. They can include removing the stent and polymer coating from the mold.

In these example embodiments of first methods, dipping the stent in wet polymer can form a wet polymer coating on the stent, and placing the stent on the mold can include placing the stent with the wet polymer coating on the mold.

These example embodiments of first methods can include finishing the polymer coating to form the implantable valve. The implantable valve can be in accordance with any of the aforementioned valve embodiments.

In many example embodiments, second methods of manufacturing an implantable valve are provided, where the second methods include: forming a polymeric valvular body; positioning the polymeric valvular body over a stent; dipping an upstream portion of the stent and polymeric valvular body in wet polymer such that a polymer coating is placed on the upstream portion; and allowing the polymer coating to cure.

In these example embodiments of second methods, forming the polymeric valvular body can include: dipping a mold in wet polymer to form a polymer coating on the mold; allowing the polymer coating on the mold to cure; and trimming the valvular body to form a plurality of leaflets. The mold can include a contoured surface to form the plurality of leaflets.

These example embodiments of second methods can also include: dipping the stent in wet polymer; and allowing the dipped stent to cure, prior to positioning the polymeric valvular body over the stent.

In these example embodiments of second methods, the polymeric valvular body can be positioned over the stent such that the stent is aligned with the plurality of leaflets. The polymeric valvular body can be positioned over the stent such that commissure positions between adjacent leaflets are aligned with corresponding positions on the stent.

In these example embodiments of second methods, the valvular body can include a plurality of leaflets, and the upstream portion of the stent and polymeric valvular body can be dipped in wet polymer such that the polymer coating is placed on the upstream portion and not on the plurality of leaflets.

In these example embodiments of second methods, allowing the polymer coating to cure can include allowing the polymer coating to cure while an upstream end of the valvular body is facing downward.

In these example embodiments of second methods, the implantable valve can be formed after allowing the polymer coating to cure or after performing valve finishing to the stent or valvular body. The implantable valve can be in accordance with any of the aforementioned valve embodiments.

In many example embodiments, third methods of manufacturing an implantable valve are provided, where the third methods include: forming a polymeric valvular body; dipping a stent in wet polymer; positioning the stent having wet polymer thereon over the polymeric valvular body; dipping an upstream portion of the stent and polymeric valvular body in wet polymer such that a polymer coating is placed on the upstream portion; and allowing the polymer coating to cure.

In these example embodiments of third methods, forming the polymeric valvular body can include: dipping a mold in wet polymer to form a polymer coating on the mold; and allowing the polymer coating on the mold to cure. The mold can include a contoured surface to form the plurality of leaflets.

In these example embodiments of third methods, the stent can be positioned over the valvular body such that the stent is aligned with a plurality of leaflets of the valvular body. The stent can be positioned over the polymeric valvular body such that commissure positions between adjacent leaflets of the polymeric valvular body are aligned with corresponding positions on the stent.

In these example embodiments of third methods, the valvular body can include a plurality of leaflets, and the upstream portion of the stent and polymeric valvular body are dipped in wet polymer such that the polymer coating is placed on the upstream portion and not on the plurality of leaflets.

In these example embodiments of third methods, allowing the polymer coating to cure can include allowing the polymer coating to cure while an upstream end of the valvular body is facing downward.

In these example embodiments of third methods, the implantable valve can be formed after allowing the polymer coating to cure or after performing valve finishing to the stent or valvular body. The implantable valve can be in accordance with any of the aforementioned valve embodiments.

In many example embodiments, fourth methods of manufacturing an implantable valve are provided, where the fourth methods include: dipping a mold in wet polymer to form a polymer coating in a wet state; dipping a stent in wet polymer; positioning the stent having wet polymer thereon over the polymer coating in the wet state; and allowing the stent and polymer coating to cure.

In these example embodiments of fourth methods, the mold can include a contoured surface to form a plurality of leaflets. The stent can be positioned over the polymer coating in the wet state such that the stent is aligned with the contoured surface of the mold.

In these example embodiments of fourth methods, allowing the polymer coating to cure can include allowing the polymer coating to cure while a downstream end of the mold is facing upward.

In these example embodiments of fourth methods, the implantable valve can be formed after allowing the polymer coating to cure or after performing valve finishing to the stent or valvular body. The implantable valve can be in accordance with any of the aforementioned valve embodiments.

In many example embodiments, fifth methods of manufacturing an implantable valve are provided, where the fifth methods include: positioning a stent over a polymeric valvular body; and bonding the stent to the polymeric valvular body.

These example embodiments of fifth methods can further include forming the polymeric valvular body prior to positioning the stent over the polymeric valvular body. Forming the polymeric valvular body can include: dipping a mold in wet polymer; and allowing the wet polymer on the mold to cure. The mold can include a contoured surface to form the plurality of leaflets.

These example embodiments of fifth methods can further include: dipping the stent in wet polymer; and allowing the wet polymer to cure prior to positioning the stent over the polymeric valvular body.

In these example embodiments of fifth methods, the stent can be positioned over the valvular body such that the stent is aligned with a plurality of leaflets of the valvular body. The stent can be positioned over the polymeric valvular body such that commissure positions between adjacent leaflets of the polymeric valvular body are aligned with corresponding positions on the stent.

In these example embodiments of fifth methods, bonding the stent to the polymeric valvular body can be performed with one of the following: polymeric bonding, solvent bonding, plasma bonding, or ultrasonic welding.

In these example embodiments of fifth methods, the implantable valve can be formed after allowing the polymer coating to cure or after performing valve finishing to the stent or valvular body. The implantable valve can be in accordance with any of the aforementioned valve embodiments.

In many example embodiments, sixth methods of manufacturing an implantable valve are provided, where the sixth methods include: dipping a stent in wet polymer; positioning a polymeric valvular body within the stent having wet polymer thereon; positioning a skirt of the polymeric valvular body over the stent having wet polymer thereon; and allowing the wet polymer to cure.

These example embodiments of sixth methods, can further include forming the polymeric valvular body prior to dipping the stent in wet polymer. Forming the polymeric valvular body can include: dipping a mold in wet polymer; and allowing the wet polymer on the mold to cure. These example embodiments of sixth methods, can further include trimming a plurality of leaflets on the valvular body. The polymeric valvular body can be positioned within the stent having wet polymer thereon while the polymeric valvular body is on the mold. The valvular body is positioned within the stent such that the stent is aligned with a plurality of leaflets of the valvular body. The polymeric valvular body can be positioned within the stent such that commissure positions between adjacent leaflets of the polymeric valvular body are aligned with corresponding positions on the stent.

These example embodiments of sixth methods, can further include placing a debonding shim between the skirt and the stent.

In these example embodiments of sixth methods, allowing the wet polymer to cure can include: placing the polymeric valvular body and stent within an outer mandrel.

These example embodiments of sixth methods can further include placing a tensioning element over the skirt after the skirt is positioned over the stent. The tensioning element can be placed over the skirt after the skirt is positioned over the stent and prior to allowing the wet polymer to cure.

In these example embodiments of sixth methods, the implantable valve can be formed after allowing the wet polymer to cure or after performing valve finishing to the stent or valvular body. The implantable valve can be in accordance with any of the aforementioned valve embodiments.

In many example embodiments, seventh methods of manufacturing an implantable valve are provided, where the seventh methods include: positioning a polymeric valvular body within a stent; at least partially radially contracting the stent; positioning a skirt of the polymeric valvular body over the stent while at least partially radially contracted; and allowing the stent to expand.

These example embodiments of seventh methods can further include forming the polymeric valvular body prior to positioning the polymeric valvular body within the stent. Forming the polymeric valvular body can include: dipping a mold in wet polymer; and allowing the wet polymer on the mold to cure. These example embodiments of seventh methods can further include trimming a plurality of leaflets on the valvular body.

In these example embodiments of seventh methods, the polymeric valvular body can be positioned within the stent while the polymeric valvular body is on the mold. The valvular body can be positioned within the stent such that the stent is aligned with a plurality of leaflets of the valvular body. The polymeric valvular body can be positioned within the stent such that commissure positions between adjacent leaflets of the polymeric valvular body are aligned with corresponding positions on the stent.

These example embodiments of seventh methods can further include coating the stent in polymer before positioning the polymeric valvular body within the stent.

These example embodiments of seventh methods can further include: dipping the stent in wet polymer; and allowing the wet polymer to cure before positioning the polymeric valvular body within the stent.

These example embodiments of seventh methods can further include placing a debonding shim between the skirt and the stent.

In these example embodiments of seventh methods, at least partially radially contracting the stent can include placing the polymeric valvular body and stent within an outer mandrel. Allowing the stent to expand can include removing the stent from the outer mandrel.

These example embodiments of seventh methods can further include placing a tensioning element over the skirt after the skirt is positioned over the stent.

In these example embodiments of seventh methods, the implantable valve can be formed after allowing the stent to expand or after performing valve finishing to the stent or valvular body. The implantable valve can be in accordance with any of the aforementioned valve embodiments.

In many example embodiments, eighth methods of manufacturing an implantable valve are provided, where the eighth methods include: positioning a polymeric valvular body over at least a portion of a stent such that a portion of the polymeric valvular body having a plurality of leaflets extends past the stent; and inverting the portion of the polymeric valvular body such that the plurality of leaflets are positioned within the stent.

These example embodiments of eighth methods can further include forming the polymeric valvular body prior to positioning the polymeric valvular body over the stent. Forming the polymeric valvular body can include: dipping a mold in wet polymer; and allowing the wet polymer on the mold to cure. These example embodiments of eighth methods can further include trimming a plurality of leaflets on the valvular body.

These example embodiments of eighth methods can further include coating the stent in polymer before positioning the polymeric valvular body over at least the portion of the stent.

These example embodiments of eighth methods can further include: dipping the stent in wet polymer; and allowing the wet polymer to cure before positioning the polymeric valvular body over the at least the portion of the stent.

In these example embodiments of eighth methods, the polymeric valvular body can be positioned over the at least the portion of the stent such that the plurality of leaflets are aligned with the stent. The polymeric valvular body can be positioned over the at least the portion of the stent such that commissure positions between adjacent ones of the plurality of leaflets are aligned with corresponding positions on the stent.

These example embodiments of eighth methods can further include placing a tensioning element over the polymeric valvular body.

In these example embodiments of eighth methods, the implantable valve is formed after inverting the portion of the polymeric valvular body or after performing valve finishing to the stent or valvular body. The implantable valve can be in accordance with any of the aforementioned valve embodiments.

In many example embodiments, ninth methods of manufacturing an implantable valve are provided, where the ninth methods include: inserting an upstream end of a mold into a stent; dipping the mold and stent into wet polymer to form a polymer coating; allowing the polymer coating to cure to form a valvular body; removing the valvular body and stent from the mold; and inverting a downstream side of the valvular body into the stent.

These example embodiments of ninth methods can further include applying a restraining band over an exterior of the stent and mold prior to dipping the mold and stent into wet polymer.

In these example embodiments of ninth methods, allowing the polymer coating to cure to form a valvular body can include allowing the polymer coating to cure while a downstream end of the mold is facing downward.

These example embodiments of ninth methods can further include trimming a plurality of leaflets on the downstream side of the valvular body prior to removing the valvular body and stent from the mold.

These example embodiments of ninth methods can further include coating the stent in polymer before inserting the upstream end of the mold into the stent.

These example embodiments of ninth methods can further include: dipping the stent in wet polymer; and allowing the wet polymer to cure before inserting the upstream end of the mold into the stent.

In these example embodiments of ninth methods, inserting the upstream end of the mold into the stent can include aligning draft angle positions on the mold with corresponding positions on the stent.

In these example embodiments of ninth methods, the implantable valve can be formed after inverting the downstream side of the valvular body into the stent or after performing valve finishing to the stent or valvular body. The implantable valve can be in accordance with any of the aforementioned valve embodiments.

Those of ordinary skill in the art will readily recognize, in light of this description, the many variations of suitable dip casting procedures, pressures, and temperatures that are not stated here yet are suitable to fabricate the prosthetic heart valves described herein. Likewise, those of ordinary skill in the art will also recognize, in light of this description, the alternatives to dip casting that can be used to fabricate the prosthetic heart valves described herein.

As used herein and in the appended claims, the singular forms "a", "an", and "the" include plural referents unless the context clearly dictates otherwise.

Where a range of values is provided, each intervening value, to the tenth of the unit of the lower limit unless the context clearly dictates otherwise, between the upper and lower limit of that range and any other stated or intervening value in that stated range, is encompassed within the disclosure and can be claimed as a sole value or as a smaller range. Where the stated range includes one or both of the limits, ranges excluding either or both of those included limits are also included in the disclosure.

Where a discrete value or range of values is provided, that value or range of values may be claimed more broadly than as a discrete number or range of numbers, unless indicated otherwise. For example, each value or range of values provided herein may be claimed as an approximation and this paragraph serves as antecedent basis and written support for the introduction of claims, at any time, that recite each such value or range of values as "approximately" that value, "approximately" that range of values, "about" that value, and/or "about" that range of values. Conversely, if a value or range of values is stated as an approximation or generalization, e.g., approximately X or about X, then that value or range of values can be claimed discretely without using such a broadening term.

However, in no way should this specification be interpreted as implying that the subject matter disclosed herein is limited to a particular value or range of values absent explicit recitation of that value or range of values in the claims. Values and ranges of values are provided herein merely as examples.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method of manufacturing an implantable valve, comprising:
    dipping only one end of a stent in wet polymer;
    placing the dipped stent on a mold, the mold comprising draft angle positions and a contoured surface portion adjacent to draft angle positions, wherein the dipped stent is placed on the mold such that draft angle positions are aligned with commissure positions on the stent;
    dipping the mold and dipped stent in wet polymer such that at least the contoured surface portion of the mold and at least a portion of the stent are covered in a polymer coating; and
    curing the polymer coating.

2. The method of claim 1, wherein the contoured surface portion comprises a negative image of a plurality of leaflets.

3. The method of claim 1, wherein the mold comprises a run-off portion and wherein curing the polymer coating comprises allowing wet polymer to drain along the run-off portion.

4. The method of claim 1, further comprising trimming the cured polymer coating to form a plurality of leaflets.

5. The method of claim 1, wherein the implantable valve in finished form comprises electrospun polymer located about an exterior upstream portion of the implantable valve.

6. The method of claim 1, wherein dipping the stent in wet polymer forms a wet polymer coating on the stent, and wherein placing the stent on the mold comprises placing the stent with the wet polymer coating on the mold.

7. The method of claim 1, wherein dipping the stent in wet polymer forms a wet polymer coating on the stent, and wherein the method further comprises allowing the wet polymer to cure before placing the stent on the mold.

8. The method of claim 1, wherein a same wet polymer is used for the step of dipping the stent and for the step of dipping the mold and dipped stent.

9. The method of claim 1, wherein wet polymers having different viscosities are used for the step of dipping the stent and for the step of dipping the mold and dipped stent.

10. The method of claim 1, wherein the implantable valve in finished form can transition between a contracted configuration and an expanded configuration.

11. A method of manufacturing an implantable valve, comprising:
    dipping only one end of a stent in wet polymer;
    placing the dipped stent on a mold;
    dipping the mold and dipped stent in wet polymer such that at least a portion of the mold and at least a portion of the stent are covered in a polymer coating;
    curing the polymer coating; and
    trimming the polymer coating to form a plurality of leaflets,
    wherein the implantable valve in finished form comprises electrospun polymer located about an exterior upstream portion of the implantable valve.

12. The method of claim 11, wherein the mold comprises a contoured surface portion comprises a negative image of the plurality of leaflets.

13. The method of claim 11, wherein the mold comprises a run-off portion and wherein curing the polymer coating comprises allowing wet polymer to drain along the run-off portion.

14. The method of claim 11, wherein dipping the stent in wet polymer forms a wet polymer coating on the stent, and wherein placing the stent on the mold comprises placing the stent with the wet polymer coating on the mold.

15. The method of claim 11, wherein dipping the stent in wet polymer forms a wet polymer coating on the stent, and wherein the method further comprises allowing the wet polymer to cure before placing the stent on the mold.

16. The method of claim 11, wherein a same wet polymer is used for the step of dipping the stent and for the step of dipping the mold and dipped stent.

17. The method of claim 11, wherein wet polymers having different viscosities are used for the step of dipping the stent and for the step of dipping the mold and dipped stent.

18. The method of claim 11, wherein the implantable valve in finished form can transition between a contracted configuration and an expanded configuration.

* * * * *